United States Patent
Schweitzer et al.

(10) Patent No.: US 9,726,167 B2
(45) Date of Patent: Aug. 8, 2017

(54) METHODS, CIRCUITS, DEVICES, APPARATUSES, ENCASEMENTS AND SYSTEMS FOR IDENTIFYING IF A MEDICAL INFUSION SYSTEM IS DECALIBRATED

(75) Inventors: Nimrod Schweitzer, Tel Aviv (IL); Andrei Yosef, Even Yehuda (IL); Boaz Eitan, Hofit (IL); Shaul Eitan, Hofit (IL); Meged Ofer, Netanya (IL); Shalom Sayag, Jerusalem (IL)

(73) Assignee: Q-CORE MEDICAL LTD., Netanya (IL)

( * ) Notice: Subject to any disclaimer, the term of this patent is extended or adjusted under 35 U.S.C. 154(b) by 737 days.

(21) Appl. No.: 14/126,852

(22) PCT Filed: Jun. 21, 2012

(86) PCT No.: PCT/IB2012/053149
§ 371 (c)(1),
(2), (4) Date: Dec. 17, 2013

(87) PCT Pub. No.: WO2013/001425
PCT Pub. Date: Jan. 3, 2013

(65) Prior Publication Data
US 2014/0119954 A1    May 1, 2014

Related U.S. Application Data

(60) Provisional application No. 61/457,876, filed on Jun. 27, 2011.

(51) Int. Cl.
G01F 1/12    (2006.01)
G01F 1/50    (2006.01)
(Continued)

(52) U.S. Cl.
CPC .............. *F04B 49/00* (2013.01); *A61M 5/142* (2013.01); *A61M 5/16854* (2013.01);
(Continued)

(58) Field of Classification Search
CPC .............. A61M 5/142; A61M 5/16854; A61M 5/16859; A61M 5/16886; A61M 5/365
(Continued)

(56) References Cited

U.S. PATENT DOCUMENTS 2,056,322 A    10/1936   Hoppe
2,393,838 A    1/1946    Tarbox
(Continued)

FOREIGN PATENT DOCUMENTS

DE    10118086 A1    7/2002
EP    0215249 A1     3/1987
(Continued)

OTHER PUBLICATIONS

European Application No. 05810500.8 Official Action dated Nov. 3, 2014 (5 pages).
(Continued)

*Primary Examiner* — David M Gray
*Assistant Examiner* — Geoffrey T Evans
(74) *Attorney, Agent, or Firm* — Vladimir Sherman; Professional Patent Solutions

(57) ABSTRACT

Disclosed is an infusion pump which may include a native pumping mechanism to drive fluids through a functionally associated conduit, at least one native sensor to sense a physical characteristic of the fluid within the conduit and computing circuitry having a decalibration test mode to determine whether the infusion pump is decalibrated. The computing circuitry may be adapted to receive output from at least one native sensor during the decalibration test mode.

13 Claims, 9 Drawing Sheets

(51) Int. Cl.
*G01F 25/00* (2006.01)
*G01L 27/00* (2006.01)
*F04B 49/00* (2006.01)
*A61M 5/142* (2006.01)
*A61M 5/168* (2006.01)
*A61M 5/36* (2006.01)

(52) U.S. Cl.
CPC .... *A61M 5/16859* (2013.01); *A61M 5/16886* (2013.01); *A61M 5/365* (2013.01); *A61M 2205/15* (2013.01); *A61M 2205/3331* (2013.01); *A61M 2205/3334* (2013.01); *A61M 2205/3351* (2013.01); *A61M 2205/3355* (2013.01); *A61M 2205/50* (2013.01); *A61M 2205/70* (2013.01); *A61M 2209/02* (2013.01)

(58) Field of Classification Search
USPC ........................................................ 702/100
See application file for complete search history.

(56) References Cited

U.S. PATENT DOCUMENTS

| | | | |
|---|---|---|---|
| 2,743,898 | A | 5/1956 | King |
| 2,981,115 | A | 4/1961 | Beguin |
| 3,443,585 | A | 5/1969 | Reinicke |
| 3,511,583 | A | 5/1970 | Brown |
| 3,677,667 | A | 7/1972 | Morrison |
| 3,778,195 | A | 12/1973 | Bamberg |
| 3,982,722 | A | 9/1976 | Bernard |
| 3,982,725 | A | 9/1976 | Clark |
| 4,014,318 | A | 3/1977 | Dockum et al. |
| 4,039,269 | A | 8/1977 | Pickering |
| 4,155,362 | A | 5/1979 | Jess |
| 4,178,138 | A | 12/1979 | Iles |
| 4,236,880 | A | 12/1980 | Archibald |
| 4,270,532 | A | 6/1981 | Franetzki et al. |
| 4,290,346 | A | 9/1981 | Bujan |
| 4,320,781 | A | 3/1982 | Bouvet et al. |
| 4,373,525 | A | 2/1983 | Kobayashi |
| 4,450,375 | A | 5/1984 | Siegal |
| 4,479,797 | A | 10/1984 | Kobayashi et al. |
| 4,489,863 | A | 12/1984 | Horchos et al. |
| 4,493,706 | A | 1/1985 | Borsanyi et al. |
| 4,650,469 | A | 3/1987 | Berg et al. |
| 4,671,792 | A | 6/1987 | Borsanyi |
| 4,682,135 | A | 7/1987 | Yamakawa |
| 4,690,673 | A | 9/1987 | Bloomquist |
| 4,725,205 | A | 2/1988 | Cannon et al. |
| 4,728,265 | A | 3/1988 | Cannon |
| 4,741,736 | A | 5/1988 | Brown |
| 4,748,003 | A | 5/1988 | Riley |
| 4,755,168 | A | 7/1988 | Romanelli et al. |
| 4,836,752 | A | 6/1989 | Burkett |
| 4,867,744 | A | 9/1989 | Borsanyi |
| 4,893,991 | A | 1/1990 | Heminway et al. |
| 4,927,411 | A | 5/1990 | Pastrone et al. |
| 4,954,046 | A | 9/1990 | Irvin et al. |
| 4,954,256 | A | 9/1990 | Degen et al. |
| 4,978,335 | A | 12/1990 | Arthur, III |
| 5,074,756 | A | 12/1991 | Davis |
| 5,078,683 | A | 1/1992 | Sancoff et al. |
| 5,088,904 | A | 2/1992 | Okada |
| 5,096,385 | A | 3/1992 | Georgi et al. |
| 5,103,211 | A | 4/1992 | Daoud et al. |
| 5,151,019 | A | 9/1992 | Danby et al. |
| 5,152,680 | A | 10/1992 | Okada |
| 5,165,874 | A | 11/1992 | Sancoff et al. |
| 5,213,483 | A | 5/1993 | Flaherty et al. |
| 5,219,327 | A | 6/1993 | Okada |
| 5,222,946 | A | 6/1993 | Kamen |
| 5,246,347 | A | 9/1993 | Davis |
| 5,257,978 | A | 11/1993 | Haber et al. |
| 5,286,176 | A | 2/1994 | Bonin |
| 5,290,158 | A | 3/1994 | Okada |
| 5,308,333 | A | 5/1994 | Skakoon |
| 5,338,157 | A | 8/1994 | Blomquist |
| 5,395,320 | A | 3/1995 | Padda et al. |
| 5,429,485 | A | 7/1995 | Dodge |
| 5,485,408 | A | 1/1996 | Blomquist |
| 5,499,969 | A | 3/1996 | Beuchat et al. |
| 5,509,439 | A | 4/1996 | Tantardini |
| 5,527,295 | A | 6/1996 | Wing |
| 5,542,826 | A | 8/1996 | Warner |
| 5,569,188 | A | 10/1996 | Mackool |
| 5,575,309 | A | 11/1996 | Connell |
| 5,575,631 | A | 11/1996 | Jester |
| 5,577,891 | A | 11/1996 | Loughnane et al. |
| 5,584,667 | A | 12/1996 | Davis |
| 5,593,134 | A | 1/1997 | Steber et al. |
| 5,601,420 | A | 2/1997 | Warner et al. |
| 5,628,619 | A | 5/1997 | Wilson |
| 5,658,250 | A | 8/1997 | Blomquist et al. |
| 5,658,252 | A | 8/1997 | Johnson |
| 5,660,529 | A | 8/1997 | Hill |
| 5,669,877 | A | 9/1997 | Blomquist |
| 5,683,233 | A | 11/1997 | Moubayed et al. |
| 5,695,473 | A | 12/1997 | Olsen |
| 5,704,584 | A | 1/1998 | Winterer et al. |
| 5,742,519 | A | 4/1998 | McClendon et al. |
| 5,782,805 | A | 7/1998 | Meinzer et al. |
| 5,788,669 | A | 8/1998 | Peterson |
| 5,791,880 | A | 8/1998 | Wilson |
| 5,791,881 | A | 8/1998 | Moubayed et al. |
| 5,803,712 | A | 9/1998 | Davis et al. |
| 5,807,322 | A | 9/1998 | Lindsey et al. |
| 5,810,323 | A | 9/1998 | Winterer et al. |
| 5,853,386 | A | 12/1998 | Davis et al. |
| 5,876,370 | A | 3/1999 | Blomquist |
| 5,888,052 | A | 3/1999 | Hill |
| 5,896,076 | A | 4/1999 | Van Namen |
| 5,909,724 | A | 6/1999 | Nishimura et al. |
| 5,924,852 | A | 7/1999 | Moubayed et al. |
| 5,935,099 | A | 8/1999 | Peterson et al. |
| 5,935,106 | A | 8/1999 | Olsen |
| 5,943,633 | A | 8/1999 | Wilson et al. |
| 5,954,485 | A | 9/1999 | Johnson et al. |
| 5,980,490 | A | 11/1999 | Tsoukalis |
| 5,996,964 | A | 12/1999 | Ben-Shalom |
| 6,024,539 | A | 2/2000 | Blomquist |
| 6,095,189 | A | 8/2000 | Ben-Shalom |
| 6,110,153 | A | 8/2000 | Davis et al. |
| 6,146,109 | A | 11/2000 | Davis et al. |
| 6,164,921 | A | 12/2000 | Moubayed et al. |
| 6,165,874 | A | 12/2000 | Powell et al. |
| RE37,074 | E | 2/2001 | Danby et al. |
| 6,203,296 | B1 | 3/2001 | Ray et al. |
| 6,213,723 | B1 | 4/2001 | Danby et al. |
| 6,213,739 | B1 | 4/2001 | Phallen et al. |
| 6,234,773 | B1 | 5/2001 | Hill et al. |
| 6,241,704 | B1 | 6/2001 | Peterson et al. |
| 6,261,262 | B1 | 7/2001 | Briggs et al. |
| 6,280,408 | B1 | 8/2001 | Sipin |
| 6,312,227 | B1 | 11/2001 | Davis |
| 6,339,410 | B1 | 1/2002 | Milner et al. |
| 6,347,553 | B1 | 2/2002 | Morris et al. |
| 6,371,732 | B1 | 4/2002 | Moubayed et al. |
| 6,422,057 | B1 | 7/2002 | Anderson |
| 6,450,773 | B1 | 9/2002 | Upton |
| 6,475,180 | B2 | 11/2002 | Peterson et al. |
| 6,519,569 | B1 | 2/2003 | White et al. |
| 6,537,244 | B2 | 3/2003 | Paukovits et al. |
| 6,544,171 | B2 | 4/2003 | Beetz et al. |
| 6,558,347 | B1 | 5/2003 | Jhuboo et al. |
| 6,572,604 | B1 | 6/2003 | Platt et al. |
| 6,622,542 | B2 | 9/2003 | Derek et al. |
| 6,648,861 | B2 | 11/2003 | Platt et al. |
| 6,692,241 | B2 | 2/2004 | Watanabe et al. |
| 6,733,476 | B2 | 5/2004 | Christenson et al. |
| 6,742,992 | B2 | 6/2004 | Davis |
| 6,749,587 | B2 | 6/2004 | Flaherty |
| 6,768,425 | B2 | 7/2004 | Flaherty et al. |
| 6,788,199 | B2 | 9/2004 | Crabtree et al. |
| 6,790,198 | B1 | 9/2004 | White et al. |

(56) References Cited

U.S. PATENT DOCUMENTS

| | | |
|---|---|---|
| 6,902,549 B2 | 6/2005 | Marmaropoulos et al. |
| 6,942,473 B2 | 9/2005 | Abrahamson et al. |
| 7,018,361 B2 | 3/2006 | Gillespie, Jr. et al. |
| 7,022,075 B2 | 4/2006 | Grunwald et al. |
| 7,048,720 B1 | 5/2006 | Thorne, Jr. et al. |
| 7,059,840 B2 | 6/2006 | Corwin et al. |
| 7,122,026 B2 | 10/2006 | Rogers et al. |
| 7,131,966 B1 | 11/2006 | Tamari |
| 7,163,385 B2 | 1/2007 | Gharib et al. |
| 7,347,836 B2 | 3/2008 | Peterson et al. |
| 7,525,432 B2 | 4/2009 | Jackson |
| 7,556,481 B2 | 7/2009 | Moubayed |
| 7,645,258 B2 | 1/2010 | White et al. |
| 7,654,976 B2 | 2/2010 | Peterson et al. |
| 7,695,255 B2 | 4/2010 | Ben-Shalom et al. |
| 7,698,156 B2 | 4/2010 | Martucci et al. |
| 7,704,227 B2 | 4/2010 | Moberg et al. |
| 7,762,795 B2 | 7/2010 | Moubayed |
| 7,840,260 B2 | 11/2010 | Epley |
| 7,892,332 B2 | 2/2011 | Prisco et al. |
| 7,896,834 B2 | 3/2011 | Smisson, III et al. |
| 7,935,102 B2 | 5/2011 | Breznock et al. |
| 7,938,796 B2 | 5/2011 | Moubayed et al. |
| 7,963,946 B2 | 6/2011 | Moubayed et al. |
| 7,998,121 B2 | 8/2011 | Stringham |
| 8,025,634 B1 | 9/2011 | Moubayed et al. |
| 8,029,253 B2 | 10/2011 | Rotem et al. |
| 8,142,400 B2 | 3/2012 | Rotem et al. |
| 8,182,445 B2 | 5/2012 | Moubayed et al. |
| 8,197,235 B2 | 6/2012 | Davis |
| 8,214,231 B2 | 7/2012 | Martucci et al. |
| 8,234,128 B2 | 7/2012 | Martucci et al. |
| 8,241,018 B2 | 8/2012 | Harr |
| 8,257,654 B2 | 9/2012 | Maus et al. |
| 8,308,457 B2 | 11/2012 | Rotem et al. |
| 8,334,768 B2 | 12/2012 | Eaton et al. |
| 8,337,168 B2 | 12/2012 | Rotem et al. |
| 8,343,111 B2 | 1/2013 | Beck et al. |
| 8,352,290 B2 | 1/2013 | Bartz et al. |
| 8,363,583 B2 | 1/2013 | Jia et al. |
| 8,371,832 B2 | 2/2013 | Rotem et al. |
| 8,444,587 B2 | 5/2013 | Kelly et al. |
| 8,489,427 B2 | 7/2013 | Simpson et al. |
| 8,535,025 B2 | 9/2013 | Rotem et al. |
| 8,579,816 B2 | 11/2013 | Kamath et al. |
| 8,666,367 B2 | 3/2014 | Sharp et al. |
| 8,672,875 B2 | 3/2014 | Vanderveen et al. |
| 8,678,793 B2 | 3/2014 | Goldor et al. |
| 8,920,144 B2 | 12/2014 | Rotem et al. |
| 9,056,160 B2 | 6/2015 | Rotem et al. |
| 2001/0029321 A1 | 10/2001 | Beetz et al. |
| 2002/0056675 A1 | 5/2002 | Hegde |
| 2002/0094287 A1 | 7/2002 | Davis |
| 2002/0156402 A1 | 10/2002 | Woog et al. |
| 2002/0165503 A1 | 11/2002 | Morris et al. |
| 2003/0034887 A1 | 2/2003 | Crabtree et al. |
| 2003/0040700 A1 | 2/2003 | Hickle et al. |
| 2003/0065536 A1 | 4/2003 | Hansen et al. |
| 2003/0109988 A1 | 6/2003 | Geissler et al. |
| 2003/0140928 A1 | 7/2003 | Bui et al. |
| 2003/0141981 A1 | 7/2003 | Bui et al. |
| 2003/0182586 A1 | 9/2003 | Numano |
| 2004/0167804 A1 | 8/2004 | Simpson et al. |
| 2004/0172222 A1 | 9/2004 | Simpson et al. |
| 2004/0181314 A1 | 9/2004 | Zaleski |
| 2004/0191112 A1 | 9/2004 | Hill et al. |
| 2004/0204673 A1 | 10/2004 | Flaherty |
| 2004/0204685 A1 | 10/2004 | Wright et al. |
| 2004/0235446 A1 | 11/2004 | Flaherty et al. |
| 2005/0001369 A1 | 1/2005 | Cross |
| 2005/0022274 A1 | 1/2005 | Campbell et al. |
| 2005/0055242 A1 | 3/2005 | Bello et al. |
| 2005/0088409 A1 | 4/2005 | Van Berkel |
| 2005/0112001 A1 | 5/2005 | Bahnen et al. |
| 2005/0171501 A1 | 8/2005 | Kelly |
| 2005/0191196 A1 | 9/2005 | Tanner et al. |
| 2005/0214146 A1 | 9/2005 | Corwin et al. |
| 2006/0051218 A1 | 3/2006 | Harttig |
| 2006/0083644 A1 | 4/2006 | Zumbrum et al. |
| 2006/0173419 A1 | 8/2006 | Malcolm |
| 2006/0213249 A1 | 9/2006 | Uram et al. |
| 2007/0032098 A1 | 2/2007 | Bowles et al. |
| 2007/0048161 A1 | 3/2007 | Moubayed |
| 2007/0060872 A1 | 3/2007 | Hall et al. |
| 2007/0118405 A1 | 5/2007 | Campbell et al. |
| 2007/0135866 A1 | 6/2007 | Baker et al. |
| 2007/0154336 A1 | 7/2007 | Miyazaki et al. |
| 2007/0217931 A1 | 9/2007 | Estes et al. |
| 2007/0269324 A1 | 11/2007 | Goldor et al. |
| 2008/0015506 A1 | 1/2008 | Davis |
| 2008/0065007 A1 | 3/2008 | Peterson et al. |
| 2008/0065016 A1 | 3/2008 | Peterson et al. |
| 2008/0067462 A1 | 3/2008 | Miller et al. |
| 2008/0071251 A1 | 3/2008 | Moubayed et al. |
| 2008/0095649 A1 | 4/2008 | Ben-Shalom et al. |
| 2008/0144560 A1 | 6/2008 | Jia et al. |
| 2008/0145249 A1 | 6/2008 | Smisson et al. |
| 2008/0146995 A1 | 6/2008 | Smisson et al. |
| 2008/0275307 A1 | 11/2008 | Poschmann |
| 2009/0031797 A1* | 2/2009 | Das .......... G01F 1/007 73/227 |
| 2009/0088675 A1 | 4/2009 | Kelly et al. |
| 2009/0163864 A1 | 6/2009 | Breznock et al. |
| 2009/0203329 A1 | 8/2009 | White et al. |
| 2009/0221964 A1 | 9/2009 | Rotem et al. |
| 2009/0240201 A1 | 9/2009 | Rotem et al. |
| 2009/0270810 A1 | 10/2009 | DeBelser et al. |
| 2009/0300507 A1 | 12/2009 | Raghavan et al. |
| 2009/0317268 A1 | 12/2009 | Rotem et al. |
| 2010/0016781 A1 | 1/2010 | Nakayama et al. |
| 2010/0036322 A1 | 2/2010 | Rotem |
| 2010/0082001 A1 | 4/2010 | Beck et al. |
| 2010/0168545 A1 | 7/2010 | Kamath et al. |
| 2010/0211002 A1 | 8/2010 | Davis |
| 2010/0218586 A1* | 9/2010 | Rosinko ............ G01F 11/08 73/1.35 |
| 2010/0228223 A1 | 9/2010 | Williams et al. |
| 2010/0234708 A1 | 9/2010 | Buck et al. |
| 2010/0279652 A1 | 11/2010 | Sharp et al. |
| 2011/0148624 A1 | 6/2011 | Eaton et al. |
| 2011/0152772 A1 | 6/2011 | Rotem et al. |
| 2011/0152831 A1 | 6/2011 | Rotem et al. |
| 2011/0167133 A1 | 7/2011 | Jain |
| 2011/0251856 A1 | 10/2011 | Maus et al. |
| 2011/0264043 A1 | 10/2011 | Kotnik et al. |
| 2011/0276000 A1 | 11/2011 | Stringham |
| 2011/0282291 A1 | 11/2011 | Ciccone |
| 2011/0318208 A1 | 12/2011 | Goldor et al. |
| 2012/0059389 A1 | 3/2012 | Larson et al. |
| 2012/0062387 A1 | 3/2012 | Vik et al. |
| 2012/0136305 A1 | 5/2012 | Gagliardoni et al. |
| 2012/0241525 A1 | 9/2012 | Borges et al. |
| 2013/0006666 A1 | 1/2013 | Schneider et al. |
| 2013/0046508 A1 | 2/2013 | Sur et al. |
| 2013/0116620 A1 | 5/2013 | Rotem et al. |
| 2013/0116623 A1 | 5/2013 | Rotem et al. |
| 2013/0142670 A1 | 6/2013 | Rotem et al. |
| 2013/0209275 A1 | 8/2013 | Rotem et al. |
| 2013/0279370 A1 | 10/2013 | Eitan et al. |
| 2013/0345623 A1 | 12/2013 | Kopperschmidt et al. |
| 2014/0005631 A1 | 1/2014 | Rotem et al. |
| 2014/0119954 A1 | 5/2014 | Schweitzer et al. |
| 2014/0197824 A1 | 7/2014 | Gillespie et al. |
| 2014/0222377 A1 | 8/2014 | Bitan et al. |
| 2014/0276564 A1 | 9/2014 | Schneider |
| 2014/0369872 A1 | 12/2014 | Goldor et al. |
| 2014/0378901 A1 | 12/2014 | Rotem et al. |
| 2015/0038187 A1 | 2/2015 | Ho et al. |
| 2015/0073338 A1 | 3/2015 | Waldhoff et al. |
| 2015/0105726 A1 | 4/2015 | Qi et al. |
| 2015/0122052 A1* | 5/2015 | Rosinko ............ A61M 5/16854 73/861.42 |
| 2015/0137988 A1 | 5/2015 | Gravenstein et al. |
| 2015/0141955 A1 | 5/2015 | Ruchti et al. |

(56) References Cited

U.S. PATENT DOCUMENTS

| | | |
|---|---|---|
| 2015/0172921 A1 | 6/2015 | Wang et al. |
| 2015/0182694 A1 | 7/2015 | Rosinko |
| 2015/0192120 A1 | 7/2015 | Rotem et al. |

FOREIGN PATENT DOCUMENTS

| | | |
|---|---|---|
| EP | 0225158 A2 | 6/1987 |
| EP | 0315312 A1 | 5/1989 |
| EP | 0429866 A1 | 6/1991 |
| EP | 0483794 A1 | 5/1992 |
| EP | 0858812 A2 | 8/1998 |
| EP | 1031358 A1 | 8/2000 |
| EP | 1350955 A2 | 10/2003 |
| EP | 1557186 | 7/2005 |
| EP | 1611834 A2 | 1/2006 |
| EP | 1485149 B1 | 7/2008 |
| FR | 2632529 A1 | 12/1989 |
| FR | 2753236 A1 | 3/1998 |
| JP | 60043188 A | 3/1985 |
| JP | 6-169992 A | 6/1994 |
| JP | 2002-57738 A | 2/2002 |
| JP | 2004141418 A | 5/2004 |
| WO | 8400691 A1 | 3/1984 |
| WO | 9116933 A1 | 11/1991 |
| WO | 9325816 A1 | 12/1993 |
| WO | 9408647 A1 | 4/1994 |
| WO | 9603168 A1 | 2/1996 |
| WO | 9630679 A1 | 10/1996 |
| WO | 9734084 A1 | 9/1997 |
| WO | 9804301 A1 | 2/1998 |
| WO | 9813080 A2 | 4/1998 |
| WO | 9847551 A1 | 10/1998 |
| WO | 99/58178 A1 | 11/1999 |
| WO | 0139816 A2 | 6/2001 |
| WO | 0165232 A1 | 9/2001 |
| WO | 0236044 A2 | 5/2002 |
| WO | 0238204 A2 | 5/2002 |
| WO | 0249509 A2 | 6/2002 |
| WO | 02068015 A2 | 9/2002 |
| WO | 03027503 A1 | 4/2003 |
| WO | 03080158 A1 | 10/2003 |
| WO | 2004070548 A2 | 8/2004 |
| WO | 2004093648 A2 | 11/2004 |
| WO | 2005089263 A2 | 9/2005 |
| WO | 2006/056986 A1 | 6/2006 |
| WO | 2007133259 A1 | 11/2007 |
| WO | 2008036658 A2 | 3/2008 |
| WO | 2008059492 A2 | 5/2008 |
| WO | 2008059493 A2 | 5/2008 |
| WO | 2008059494 A2 | 5/2008 |
| WO | 2008059495 A2 | 5/2008 |
| WO | 2008059496 A2 | 5/2008 |
| WO | 2008059498 A2 | 5/2008 |
| WO | 2008059499 A2 | 5/2008 |
| WO | 2008130644 A1 | 10/2008 |
| WO | 2010053702 A1 | 5/2010 |
| WO | 2010053703 A1 | 5/2010 |
| WO | 2010091313 A2 | 8/2010 |
| WO | 2011128850 A2 | 10/2011 |
| WO | 2012095827 A1 | 7/2012 |
| WO | 2012095829 A2 | 7/2012 |
| WO | 2013001425 A2 | 1/2013 |
| WO | 2013/028704 A1 | 2/2013 |
| WO | 2013/090748 A1 | 6/2013 |

OTHER PUBLICATIONS

European Application No. 05810500.8 Response to Official Action dated Nov. 3, 2014, submitted Mar. 9, 2015 (31 pages).
Indian Patent Application No. 2344KOLNP2007 Office Action dated Dec. 31, 2014 (2 pages).
Indian Patent Application No. 2344KOLNP2007 Response to Office Action dated Dec. 31, 2014, submitted Aug. 7, 2015 (19 pages).
U.S. Appl. No. 14/181,673 Official Action (Non-Final) dated Jun. 3, 2015 (12 pages).
U.S. Appl. No. 13/651,420 Official Action (Final) dated Mar. 16, 2015 (6 pages).
U.S. Appl. No. 13/651,420 Response to Official Action (Final) dated Mar. 16, 2015, submitted May 14, 2015 (5 pages).
U.S. Appl. No. 13/651,420 Official Action (Final) dated Jun. 9, 2015 (9 pages).
U.S. Appl. No. 14/016,105 Response to Official Action (Non-Final) dated Oct. 15, 2014, submitted Jan. 14, 2015 (7 pages).
U.S. Appl. No. 14/016,105 Notice of Allowance dated Feb. 17, 2015 (14 pages).
U.S. Appl. No. 13/681,440 Response to Official Action (Non-Final) dated Sep. 2, 2014, submitted Feb. 25, 2015 (12 pages).
U.S. Appl. No. 13/681,440 Official Action (Final) dated Apr. 24, 2015 (21 pages).
U.S. Appl. No. 12/514,311 Response to Official Action (Non-Final) dated Oct. 7, 2014, submitted Jan. 7, 2015 (5 pages).
U.S. Appl. No. 12/514,311 Official Action (Final) dated Apr. 20, 2015 (12 pages).
U.S. Appl. No. 12/514,311 Response to Official Action (Final) dated Apr. 20, 2015, submitted Jun. 21, 2015 (10 pages).
U.S. Appl. No. 12/514,311 Official Action (Advisory Action) dated Jul. 1, 2015 (8 pages).
U.S. Appl. No. 12/514,311 Response to Official Action (Advisory Action) dated Jul. 1, 2015, submitted Jul. 20, 2015 (8 pages).
U.S. Appl. No. 12/514,311 Official Action (Advisory Action) dated Aug. 5, 2015 (6 pages).
European Application No. 10192477.7 Official Action dated Jul. 6, 2015 (5 pages).
European Application No. 11768544.6 Response to Official Action dated Dec. 2, 2014, submitted May 29, 2015 (12 pages).
U.S. Appl. No. 13/640,519 Response to Official Action (Final) dated Oct. 1, 2014, submitted Dec. 28, 2014 (15 pages).
U.S. Appl. No. 13/640,519 Official Action (Non-Final) dated May 6, 2015 (13 pages).
European Application No. 12734200.4 Response to Official Communication dated Sep. 4, 2014, submitted Mar. 4, 2015 (16 pages).
U.S. Appl. No. 13/978,538 Official Action (Non-Final) dated Jan. 23, 2015 (24 pages).
U.S. Appl. No. 13/978,538 Response to Official Action (Non-Final) dated Jan. 23, 2015, submitted May 21, 2015 (13 pages).
U.S. Appl. No. 13/978,538 Official Action (Non-Final) dated Jul. 24, 2015 (16 pages).
European Application No. 12805094.5 Supplementary Partial European Search Report dated Feb. 23, 2015 (8 pages).
European Application No. 12805094.5 Response to Supplementary Partial European Search Report submitted Apr. 2, 2015 (1 page).
European Application No. 12805094.5 Supplementary European Search Report dated Jun. 30, 2015 (14 pages).
U.S. Appl. No. 13/924,572 Response to Official Action (Non-Final) dated Dec. 2, 2014, submitted Mar. 26, 2015 (11 pages).
U.S. Appl. No. 13/924,572 Official Action (Non-Final) dated May 14, 2015 (12 pages).
PCT Appl. No. PCT/IB14/62106 International Search Report and Written Opinion dated Feb. 24, 2015 (8 pages).
PCT Appl. No. PCT/IB15/50873 International Search Report and Written Opinion dated Jun. 25, 2015 (8 pages).
U.S. Appl. No. 12/463,399 Official Action (Non-Final) dated Jul. 21, 2011 (15 pages).
U.S. Appl. No. 12/463,399 Response to Official Action (Non-Final) dated Jul. 21, 2011, submitted Oct. 21, 2011 (5 pages).
U.S. Appl. No. 12/463,399 Official Action (Final) dated Dec. 13, 2011 (7 pages).
U.S. Appl. No. 12/463,399 Response to Official Action (Final) dated Dec. 13, 2011, submitted Feb. 12, 2012 (10 pages).
U.S. Appl. No. 12/463,399 Advisory Action and Applicant Initiated Interview Summary dated Mar. 8, 2012 (8 pages).
U.S. Appl. No. 12/463,399 Response to Official Action (Final) dated Dec. 13, 2011, submitted Mar. 26, 2012 with Request for Continued Examination (13 pages).
U.S. Appl. No. 12/463,399 Notice of Allowance issued Apr. 29, 2013 (14 pages).

(56) References Cited

OTHER PUBLICATIONS

U.S. Appl. No. 12/514,310 Official Action (Non-Final) dated Jul. 21, 2011 (8 pages).
U.S. Appl. No. 12/514,310 Response to Official Action (Non-Final) dated Jul. 21, 2011, submitted Oct. 21, 2011 (8 pages).
U.S. Appl. No. 12/514,310 Official Action (Final) dated Jan. 20, 2012 (10 pages).
U.S. Appl. No. 12/514,310 Response to Official Action (Final) dated Jan. 20, 2012, submitted Apr. 25, 2012 with Request for Continued Examination (11 pages).
U.S. Appl. No. 12/514,310 Official Action (Non-Final) dated May 25, 2012 (7 pages).
U.S. Appl. No. 12/514,310 Response to Official Action (Non-Final) dated May 25, 2012, submitted Jun. 28, 2012 (6 pages).
U.S. Appl. No. 12/514,310 Notice of Allowance issued Aug. 22, 2012 (7 pages).
U.S. Appl. No. 12/514,311 Official Action (Non-Final) dated Sep. 16, 2010 (10 pages).
U.S. Appl. No. 12/514,311 Response to Official Action (Non-Final) dated Sep. 16, 2010, submitted Dec. 9, 2010 (23 pages).
U.S. Appl. No. 12/514,311 Official Action (Final) dated Feb. 18, 2011 (7 pages).
U.S. Appl. No. 12/514,311 Examiner Interview Summary Record dated Mar. 4, 2011 (4 pages).
U.S. Appl. No. 12/514,311 Response to Official Action (Final) dated Feb. 18, 2011, submitted Mar. 31, 2011 with Request for Continued Examination (9 pages).
European Patent Application No. 10192477.7 Search Report dated May 10, 2011 (5 pages).
European Patent Application No. 10192477.7 Response to Search Report dated May 10, 2011, submitted Dec. 28, 2011.
U.S. Appl. No. 12/644,026 Official Action (Non-Final) dated Apr. 6, 2012 (12 pages).
U.S. Appl. No. 12/644,026 Response to Official Action (Non-Final) dated Apr. 6, 2012, submitted Jul. 5, 2012 (11 pages).
U.S. Appl. No. 12/644,026 Notice of Allowance issued Oct. 11, 2012 (10 pages).
U.S. Appl. No. 13/742,454 Official Action (Non-Final) dated Oct. 7, 2013 (13 pages).
U.S. Appl. No. 12/644,027 Official Action (Non-Final) dated Apr. 28, 2011 (7 pages).
U.S. Appl. No. 12/644,027 Response to Official Action (Non-Final) dated Apr. 28, 2011, submitted Jul. 21, 2011 (10 pages).
U.S. Appl. No. 12/644,027 Notice of Allowance issued Nov. 17, 2011 (5 pages).
U.S. Appl. No. 13/229,798 Response to Official Action (Non-Final) dated Jun. 21, 2013, submitted Oct. 21, 2013 (3 pages).
U.S. Appl. No. 13/229,798 Notice of Allowance issued Nov. 14, 2013 (54 pages).
U.S. Appl. No. 13/651,420 Official Action (Non-Final) dated Nov. 4, 2013 (8 pages).
U.S. Appl. No. 13/651,420 Response to Official Action (Non-Final) dated Nov. 4, 2013, submitted Nov. 21, 2013 (2 pages).
U.S. Appl. No. 13/681,440 Official Action (Non-Final) dated Oct. 24, 2013 (11 pages).
Honeywell Sensing and Control, "FSSI500NSB force sensor", Golden Valley, Minnesota, USA, 1998-2004 http://sccatalog.honeywell.com/imc/printfriendly.asp?FAM~force&PN~FSSI500NSB (5 pages).
International Application PCT/IL2007/001398 Search Report dated Jun. 11, 2008 (2 pages).
International Application PCT/IL2007/001398 Patentability Report dated May 19, 2009 (6 pages).
International Application PCT/IL2007/001399 Search Report dated Jun. 4, 2008 (3 pages).
International Application PCT/IL2007/001399 Patentability Report dated May 19, 2009 (9 pages).
International Application PCT/IL2007/001400 Search Report dated Jul. 15, 2008 (3 pages).
International Application PCT/IL2007/001400 Patentability Report dated May 19, 2009 (10 pages).
International Application PCT/IL2007/001401 Search Report dated Sep. 24, 2008 (2 pages).
International Application PCT/IL2007/001401 Patentability Report dated May 19, 2009 (11 pages).
International Application PCT/IL2007/001402 Search Report dated Jun. 20, 2008 (3 pages).
International Application PCT/IL2007/001402 Patentability Report dated May 19, 2009 (4 pages).
International Application PCT/IL2007/001404 Search Report dated Jul. 14, 2008 (2 pages).
International Application PCT/IL2007/001404 Patentability Report dated May 19, 2009 (7 pages).
International Application PCT/IL2007/001405 Search Report dated Jul. 21, 2008 (4 pages).
International Application PCT/IL2007/001405 Patentability Report dated May 19, 2009 (7 pages).
International Application PCT/IL2005/001249 Search Report dated Apr. 5, 2006 (18 pages).
International Application PCT/IL1997/000289 Search report dated Jan. 27, 1998 (18 pages).
International Application PCT/IL1997/000290 Search Report dated Jan. 27, 1998 (18 pages).
International Application PCT/IL2003/000947 Search Report dated Mar. 3, 2004 (43 pages).
International Application PCT/IB2011/051586 Search Report dated Oct. 27, 2011 (3 pages).
International Application PCT/IB2011/051586 Patentability Report dated Oct. 16, 2012 (9 pages).
International Application PCT/IB2012/050192 Search Report dated Aug. 17, 2012 (2 pages).
International Application PCT/IB2012/050192 Patentability Report dated Jul. 16, 2013 (6 pages).
International Application PCT/IB2012/050189 Search Report dated May 30, 2012 (2 pages).
International Application PCT/IB2012/050189 Patentability Report dated Jul. 16, 2013 (5 pages).
International Application PCT/IB2012/053149 Search Report dated Jan. 15, 2013 (2 pages).
U.S. Appl. No. 09/125,438 Official Action dated May 3, 1999 (4 pages).
U.S. Appl. No. 09/125,438 Official Action dated Jul. 15, 1999 (7 pages).
U.S. Appl. No. 10/535,103 Official Action dated Feb. 2, 2009 (9 pages).
European Application No. 05810500.8 Official Action dated Jul. 6, 2009 (5 pages).
European Application No. 05810500.8 Response to Official Action dated Jul. 6, 2009, submitted Oct. 15, 2009 (8 pages).
European Application No. 05810500.8 Official Action dated Jan. 23, 2012 (4 pages).
European Application No. 05810500.8 Response to Official Action dated Jan. 23, 2012, submitted May 22, 2012 (6 pages).
U.S. Appl. No. 11/791,599 Official Action (Non-Final) dated Aug. 19, 2010 (16 pages).
U.S. Appl. No. 11/791,599 Response to Official Action (Non-Final) dated Aug. 19, 2010, submitted Jan. 11, 2011 (8 pages).
U.S. Appl. No. 11/791,599 Official Action (Final) dated Mar. 31, 2011 (13 pages).
U.S. Appl. No. 11/791,599 Response to Official Action (Final) dated Mar. 31, 2011, submitted May 23, 2011 (7 pages).
U.S. Appl. No. 11/791,599 Notice of Allowance issued Jun. 14, 2011 (5 pages).
U.S. Appl. No. 13/229,798 Official Action (Non-Final) dated Dec. 26, 2012 (10 pages).
U.S. Appl. No. 13/229,798 Response to Official Action (Non-Final) dated Dec. 26, 2012, submitted Mar. 21, 2013 (13 pages).
U.S. Appl. No. 13/229,798 Notice of Allowance issued Apr. 19, 2013 (6 pages).
U.S. Appl. No. 13/229,798 Notice of Withdrawal from Issue dated May 13, 2013 (1 page).

(56) References Cited

OTHER PUBLICATIONS

U.S. Appl. No. 13/229,798 Official Action (Non-Final) dated Jun. 21, 2013 (6 pages).
Chinese Patent Application No. 200580045471.3 "Finger-type peristaltic pump" Official Action dated Jul. 18, 2008 and English translation thereof (7 pages).
Chinese Patent Application No. 200780041966.8 Official Action dated Jul. 13, 2010 (7 pages).
Chinese Patent Application No. 200780041966.8 Response to Official Action dated Jul. 13, 2010, as submitted (6 pages).
Chinese Patent Application No. 200780041966.8, translation of Notification of Grant, issued Jan. 28, 2011 (2 pages).
U.S. Appl. No. 12/464,202 Official Action (Non-Final) dated Oct. 3, 2011 (7 pages).
U.S. Appl. No. 12/464,202 Response to Official Action (Non-Final) dated Oct. 3, 2011, submitted Feb. 12, 2012 (12 pages).
U.S. Appl. No. 12/464,202 Notice of Allowance issued Jul. 11, 2012 (5 pages).
U.S. Appl. No. 13/651,420 Official Action (Non-Final) dated Jan. 6, 2014 (8 pages).
U.S. Appl. No. 13/651,420 Response to Official Action (Non-Final) dated Jan. 6, 2014, submitted Mar. 5, 2014 (9 pages).
U.S. Appl. No. 13/651,420 Official Action (Final) dated Apr. 24, 2014 (8 pages).
U.S. Appl. No. 13/651,420 Response to Official Action (Final) dated Apr. 24, 2014, submitted Jul. 22, 2014 with Request for Continued Examination (15 pages).
U.S. Appl. No. 13/651,420 Official Action (Non-Final) dated Aug. 19, 2014 (10 pages).
U.S. Appl. No. 13/651,420 Response to Official Action (Non-Final) dated Aug. 19, 2014, submitted Dec. 18, 2014 (7 pages).
U.S. Appl. No. 14/016,105 Official Action (Non-Final) dated Oct. 15, 2014 (10 pages).
U.S. Appl. No. 13/681,440 Response to Official Action (Non-Final) dated Oct. 24, 2013, submitted Jan. 20, 2014 (10 pages).
U.S. Appl. No. 13/681,440 Official Action (Final) dated Feb. 14, 2014 (14 pages).
U.S. Appl. No. 13/681,440 Response to Official Action (Final) dated Feb. 14, 2014, submitted Jul. 14, 2014 with Request for Continued Examination (14 pages).
U.S. Appl. No. 13/681,440 Official Action (Non-Final) dated Sep. 2, 2014 (19 pages).
U.S. Appl. No. 12/514,311 Official Action (Non-Final) dated Oct. 7, 2014 (11 pages).
U.S. Appl. No. 13/742,454 Response to Official Action (Non-Final) dated Oct. 7, 2013, submitted Jan. 6, 2014 (7 pages).
U.S. Appl. No. 13/742,454 Official Action (Final) dated Mar. 28, 2014 (14 pages).
U.S. Appl. No. 13/742,454 Response to Official Action (Final) dated Mar. 28, 2014, submitted Jun. 29, 2014 with Request for Continued Examination (10 pages).
U.S. Appl. No. 13/742,454 Notice of Allowance issued Aug. 21, 2014 (10 pages).
U.S. Appl. No. 13/640,519 Official Action (Non-Final) dated Dec. 24, 2013 (7 pages).
U.S. Appl. No. 13/640,519 Response to Official Action (Non-Final) dated Dec. 24, 2013, submitted Jan. 16, 2014 (2 pages).
U.S. Appl. No. 13/640,519 Official Action (Non-Final) dated Mar. 20, 2014 (15 pages).
U.S. Appl. No. 13/640,519 Response to Official Action (Non-Final) dated Mar. 20, 2014, submitted Jun. 17, 2014 (14 pages).
U.S. Appl. No. 13/640,519 Official Action (Final) dated Oct. 1, 2014 (11 pages).
U.S. Appl. No. 13/924,572 Official Action (Non-Final) dated Dec. 2, 2014 (13 pages).
European Application No. 11768544.6 Supplementary Partial European Search Report dated Nov. 13, 2014 (7 pages).
European Application No. 12734200.4 Supplementary European Search Report dated Aug. 18, 2014 (6 pages).

\* cited by examiner

METHODS, CIRCUITS, DEVICES, APPARATUSES, ENCASEMENTS AND SYSTEMS FOR IDENTIFYING IF A MEDICAL INFUSION SYSTEM IS DECALIBRATED

FIELD OF THE INVENTION

The present invention relates generally to the field of detecting infusion system decalibration. More specifically, the present invention relates to methods, circuits, devices, apparatuses and associated computer executable code for detecting infusion system decalibration and recalibration or self-calibration of infusion systems based on decalibration test results.

BACKGROUND

Medical devices operate for therapeutic and/or diagnostic uses. Some exemplary medical devices may include: blood pressure monitors which may monitor a patient's blood pressure and heart rate, electrical thermometers which may measure a patient's body temperature and many more.

Some medical devices may administer fluid to a patient via a conduit such as a flexible tube. Some medical devices may monitor fluid flowing through its system and connected to one or more of a patient's bodily fluids. For example peristaltic pumps which may be used to infuse medicines into a vein. In another example, a dialysis machine may pass a patient's blood through the machine to filter and get rid of toxins and excess fluids.

Some medical devices administering fluid or monitoring fluid may want to control the rate at which the fluid is flowing within the system. In some medical devices a flow rate may be achieved by carrying out preliminary tests on the medical device to correlate an expected flow rate to secondary features of the medical device such as motor rate and more.

A medical device may be used in a hospital, doctor or nurse's office or other medical treatment centers. Medical devices may also be used at patient's homes or personal environments.

Medical devices may require periodic recalibration to ensure that the medical device is operating properly, for example meeting predefined criteria or operating as expected.

Medical devices, including pumping systems, may be periodically recalibrated at an off-site lab by a technician or otherwise authorized personnel. Such a recalibration process may cause the medical device to be out of service for several days or weeks until returned from an off-site lab.

SUMMARY OF THE INVENTION

The present invention includes methods, circuits, devices, apparatus, encasements and systems for periodically identifying if a medical infusion pumping system has gone out of a predefined calibration range or has become decalibrated.

The present invention includes an infusion system including a native pumping mechanism to drive fluids through a functionally associated conduit, at least one native sensor to sense a physical characteristic of the fluid within the conduit; and computing circuitry having a decalibration test mode to determine if an infusion system is not within a predetermined allowable range, and adapted to receive output from said at least one native sensor during the decalibration testing.

According to some embodiments, the infusion system may include a native computing circuitry having a decalibration testing mode for facilitating detection of a decalibrated state/condition of the pump.

According to some embodiments, the infusion system may further include an external interface to allow connection of the infusion system to a decalibration testing device, which testing device may carry out/execute the comparisons of the output from at least one native sensor to an expected decalibration test output/parameter.

According to some embodiments, the expected decalibration test parameters may be stored in the testing device, the infusion system and/or an external database accessible by either the testing device, infusion system or both or otherwise.

According to some embodiments, the native sensor may be: a pressure sensor, a bubble detector, a flow meter, an accelerometer, temperature sensor, altitude sensor and more. A pressure sensor may detect the amount/level of pressure in the tube. A bubble detector may detect existence of air/gas bubbles above a predetermined threshold. A flow meter may determine the rate of fluid flowing through the conduit. An accelerometer may determine the acceleration and/or direction of acceleration of a pumping system. A temperature sensor may detect the temperature of fluid within the conduit. An altitude sensor may detect the altitude that the pumping system is in.

According to some embodiments exemplary decalibration test parameters may include: expected differences in sensed pressure values which may be dependent on the distance between marking on a conduit, detection of an air bubble, non-detection of an air-bubble and more.

According to some embodiments, ancillary Test Support Apparatuses may be associated with the infusion system to aid/enable/support tests for determining/detecting a decalibrated state/condition of the pump such as: a bubble injector, a fixed volume reservoir, a line pressure inducer set including a pressure inducer and a predefined line-marked conduit, a check valve one or more filters and more.

According to some embodiments, the testing may be carried out on-site periodically (annually, monthly, weekly, subsequent to an alarm in the pumping system or otherwise) and may include one or more tests with Ancillary Test Support Apparatuses and a decalibration testing appliance (PC) for carrying out the test, measuring results, identifying if the test result is out of a predefined allowed range, storing the results in said infusion system, and/or said testing device and/or relaying the results to a server and more. The computer operated sequence may require assistance by a technician or otherwise authorized personnel for activating, connecting and operating the test on the pump with the dedicated apparatus. The dedicated apparatus may be re-usable for a limited or allowed amount of iterations/tests such as 1, 5, 25 50 or otherwise.

According to some embodiments, the infusion system may be characterized by a unique identifier and/or identification. The decalibration test result of a specific infusion system may be stored within the infusion system and may be relayed to an external server. Furthermore, if an infusion system has failed a decalibration test it may be disabled so the infusion system cannot be re-used until recalibrated.

Exemplary infusion systems in accordance with some embodiments of the invention may include: peristaltic pumps, peristaltic finger pumps (finger pumps), peristaltic rotary pumps, volumetric pumps, syringe pumps, medical positive displacement pumps (positive displacement pumps), dosing pumps and more.

According to some embodiments, an infusion pump may include a native pumping mechanism to drive fluids through a functionally associated conduit, at least one native sensor to sense a physical characteristic of the fluid within the conduit and computing circuitry having a decalibration test mode to determine whether the infusion pump is decalibrated. The computing circuitry may be adapted to receive output from at least one native sensor during the decalibration test mode.

According to some embodiments, the infusion pump may further include an external interface for a decalibration testing device, which decalibration testing device may carry out/execute the comparison of the output to an expected decalibration test parameter. Optionally, the comparison may be used to compute a decalibration testing result.

According to some embodiments, the infusion pump may include one or more native sensors such as: a pressure sensor, a bubble detector, an accelerometer, a temperature sensor, an altitude sensor and/or a flow meter or otherwise. Optionally, the native sensor may be configured to detect that a predefined volume of fluid has passed through the native pumping mechanism.

According to some embodiments, a native pumping mechanism may be classified by a unique identification and the computing circuitry may be configured to store the unique identification and/or the decalibration testing result.

According to some embodiments, an infusion pump decalibration testing system may include: a pumping mechanism to drive fluids through a functionally associated conduit, at least one sensor to sense a physical characteristic of the fluid within the conduit, computing circuitry having a decalibration test mode and adapted to receive output from at least one of the native sensor(s) during the decalibration testing and compare the output to a predefined decalibration range and ancillary circuitry to activate a predetermined state on the pumping mechanism.

According to some embodiments, a predetermined state may be one or more of the following: inserting air above a predefined threshold within the pumping mechanism, external pressure on the pumping mechanism.

According to some embodiments, a predefined decalibration range may be: a look-up table of differences in pressure, expected flow rate and/or detection of bubbles or otherwise.

According to some embodiments, the ancillary circuitry may include a syringe, a check valve, a predefined line-marked conduit, a container having a known volume capacity which may be connectable to the conduit and valve or a selection of the recited elements and/or more.

According to some embodiments, software for carrying out decalibration testing on an infusion pump may include computer executable code to: (a) at least partially automatically activate a pumping mechanism and (b) receive an output from the pumping mechanism associated with a pumping mechanism native sensor;
computing circuitry to compare the output with a predefined expected decalibration test parameter and to determine a decalibration test result.

According to some embodiments, the output may be a termination signal indicating that a predetermined amount of fluid has passed through the pumping mechanism and the code may be further configured to receive a cycle number from a counter associated with the pumping mechanism and to calculate an estimated flow rate.

According to some embodiments, the cycle number may be: a number of pumping mechanism cycles completed, number of drops emitted by pumping mechanism and/or length of active time of pumping mechanism or otherwise.

According to some embodiments, the output may be two or more sensed pressure values and the predefined expected decalibration test parameter may be a look-up table of expected differences in pressure values.

According to some embodiments, the output may indicate if an air bubble was detected and the test parameter may be an air bubble detection expected result.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 1A:
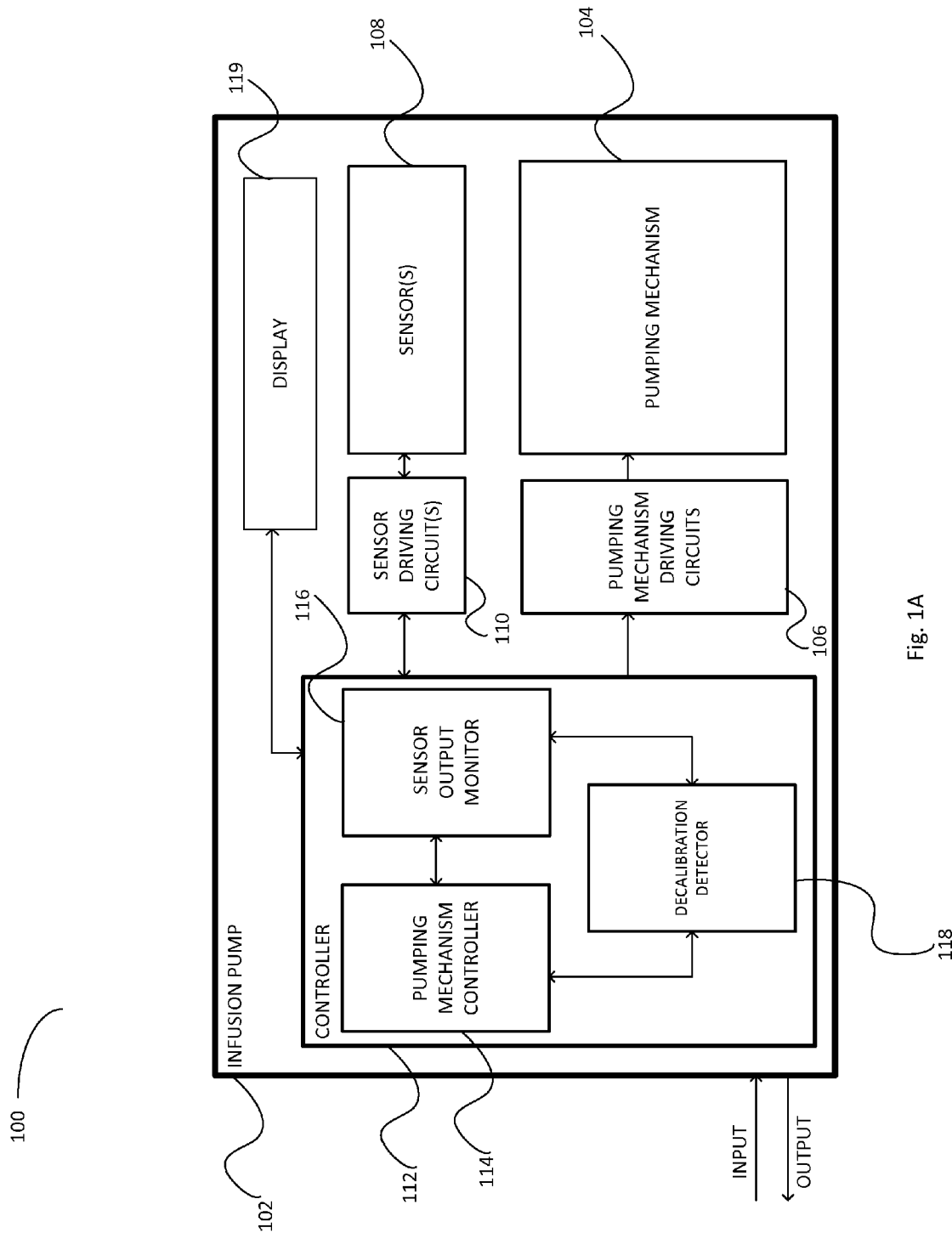
FIG. 1A is a functional block diagram of an exemplary infusion system according to some embodiments of the present invention where decalibration testing may be achieved by control circuitry integral with the pump.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION

In the following detailed description, numerous specific details are set forth in order to provide a thorough understanding of the invention. However, it will be understood by those skilled in the art that the present invention may be practiced without these specific details. In other instances, well-known methods, procedures, components and circuits have not been described in detail so as not to obscure the present invention.

Unless specifically stated otherwise, as apparent from the following discussions, it is appreciated that throughout the specification discussions utilizing terms such as "processing", "computing", "calculating", "determining", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Embodiments of the present invention may include apparatuses for performing the operations herein. This apparatus may be specially constructed for the desired purposes, or it may comprise a general purpose computer selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions, and capable of being coupled to a computer system bus.

The processes and displays presented herein are not inherently related to any particular computer or other apparatus. Various general purpose systems may be used with programs in accordance with the teachings herein, or it may prove convenient to construct a more specialized apparatus to perform the desired method. The desired structure for a variety of these systems will appear from the description below. In addition, embodiments of the present invention are not described with reference to any particular programming language. It will be appreciated that a variety of programming languages may be used to implement the teachings of the inventions as described herein.

A native element or a machine may include elements or apparatuses that are included within the machine, embedded within the machine, internal to the machine and/or used for regular operation of the machine or otherwise.

The present invention includes methods, circuits, devices, apparatus, encasements and systems for periodically identifying if a medical infusion pumping system has gone out of a predefined calibration range or has become decalibrated.

The present invention includes an infusion system including a native pumping mechanism to drive fluids through a functionally associated conduit, at least one native sensor to sense a physical characteristic of the fluid within the conduit; and computing circuitry having a decalibration test mode to determine if an infusion system is not within a predetermined allowable range, and adapted to receive output from said at least one native sensor during the decalibration testing.

According to some embodiments, the infusion system may include a native computing circuitry having a decalibration testing mode for facilitating detection of a decalibrated state/condition of the pump.

According to some embodiments, the infusion system may further include an external interface to allow connection of the infusion system to a decalibration testing device, which testing device may carry out/execute the comparisons of the output from at least one native sensor to an expected decalibration test output/parameter.

According to some embodiments, the expected decalibration test parameters may be stored in the testing device, the infusion system and/or an external database accessible by either the testing device, infusion system or both or otherwise.

According to some embodiments, the native sensor may be: a pressure sensor, a bubble detector, a flow meter, an accelerometer, temperature sensor, altitude sensor and more. A pressure sensor may detect the amount/level of pressure in the tube. A bubble detector may detect existence of air/gas bubbles above a predetermined threshold. A flow meter may determine the rate of fluid flowing through the conduit. An accelerometer may determine the acceleration and/or direction of acceleration of a pumping system. A temperature sensor may detect the temperature of fluid within the conduit. An altitude sensor may detect the altitude that the pumping system is in.

According to some embodiments exemplary decalibration test parameters may include: expected differences in sensed pressure values which may be dependent on the distance between marking on a conduit, detection of an air bubble, non-detection of an air-bubble and more.

According to some embodiments, ancillary Test Support Apparatuses may be associated with the infusion system to aid/enable/support tests for determining/detecting a decalibrated state/condition of the pump such as: a bubble injector, a fixed volume reservoir, a line pressure inducer set including a pressure inducer and a predefined line-marked conduit, a check valve one or more filters and more.

According to some embodiments, the testing may be carried out on-site periodically (annually, monthly, weekly, subsequent to an alarm in the pumping system or otherwise) and may include one or more tests with Ancillary Test Support Apparatuses and a decalibration testing appliance (PC) for carrying out the test, measuring results, identifying if the test result is out of a predefined allowed range, storing the results in said infusion system, and/or said testing device and/or relaying the results to a server and more. The computer operated sequence may require assistance by a technician or otherwise authorized personnel for activating, connecting and operating the test on the pump with the dedicated apparatus. The dedicated apparatus may be re-usable for a limited or allowed amount of iterations/tests such as 1, 5, 25 50 or otherwise.

According to some embodiments, the infusion system may be characterized by a unique identifier and/or identification. The decalibration test result of a specific infusion system may be stored within the infusion system and may be relayed to an external server. Furthermore, if an infusion system has failed a decalibration test it may be disabled so the infusion system cannot be re-used until recalibrated.

Exemplary infusion systems in accordance with some embodiments of the invention may include: peristaltic pumps, peristaltic finger pumps (finger pumps), peristaltic rotary pumps, volumetric pumps, syringe pumps, medical positive displacement pumps (positive displacement pumps), dosing pumps and more.

Turning now to FIG. 1A, depicted is a functional block diagram (100) of an exemplary infusion system, such as infusion pump 102, according to some embodiments of the present invention where decalibration testing may be achieved by control circuitry integral with the pump. Infusion pump 102 may include an electrically controllable pumping mechanism such as pumping mechanism 104. Pumping mechanism 104 may be configured to pump fluid through a tube associated with pumping mechanism 104 so that fluids are subsequently administered to a patient. Pumping mechanism 104 may be driven/operated or activated by a driving circuit such as pumping mechanism driving circuit 106 which may operate in a mechanical mode, electrical mode or combination thereof or otherwise. Infusion pump 102 may further include one or more sensors such as sensor 108 which may be configured to monitor/sense/detect a physical characteristic of the fluid flowing through a tube associated with pumping mechanism 104 or a physical characteristic associated with operation of pumping mechanism 104. The physical characteristics sensed by sensor 108 may include: presence of air bubbles higher than a predefined threshold, fluid pressure in the line/tube, flow rate, flow accuracy and/or number of cycles or time to complete a predefined criteria or counting of drops/singular volumes of fluid in a predefined time frame, acceleration of the pumping mechanism, temperature of the fluid, altitude associated characteristics and more. Sensor 108 may be driven by a driving circuit such as sensor driving circuit 110 configured to electrically activate/deactivate sensor 108. Infusion pump 102 may further include one or more functionally associated controllers such as internal controller 112. Controller 112 may be configured to control, monitor, adjust and store information associated with operation of infusion pump 102. Accordingly, controller 112 may include a pumping mechanism control (114) configured to control, activate, de-activate, adjust and more the operation of pumping mechanism 104 via pumping mechanism driving circuits 106. Controller 112 may further include a sensor output monitor (116) to receive information and/or data from the sensors and detect a physical characteristic of the fluid flowing through the associated tube. Controller 112 may further include a detector such as decalibration detector 118 configured to receive and/or store sensor output information from sensor output monitor 116 as well as predefined parameters, expected decalibration test parameters allowable ranges, pump data associated with a decalibration state and determine if infusion pump 102 is decalibrated and may emit a signal or warning if infusion pump 102 requires recalibration as well as disable infusion pump 102 if detected as decalibrated so that the pump will not be used medically until recalibrated, store the test results within infusion pump 102 and/or send an external message to an external server with the decalibration test results. Sensor output monitor 116 may further signal/relay information to pumping mechanism control 114 so that pumping mechanism control 114 may adjust driving signals to pumping mechanism 104. Decalibration detector 118 may cause the pump to recalibrate for example, by adjusting driving signals to pumping mechanism 104 or sensor 108.

According to some embodiments, infusion pump 102 may further include a display such as display 119 which may be a an electronic display such as: LCD display, LED display, touchscreen or a physical copy (such as a piece of paper) or otherwise and may be configured to be an output device to display messages and information from controller 112. According to some embodiments, display 119 may also serve as an input device to receive input information from a user or technician and relay the received information or parameters to controller 112.

According to some embodiments, during a standby mode, pumping mechanism 104, sensor 108, pumping mechanism driving circuits 106 and sensor driving circuits 110 may be disabled. Controller 112 may be in a standby or low-power mode and may await an initiation or start input.

According to some embodiments, during an operation programming and initiation mode controller 112 may receive operation parameters such as flow rate, total amount of fluid to be administered via an associated tube, length of treatment and/or otherwise. Pumping mechanism control 114 may receive information associated with the operation point parameters such as duty cycle of pump operation and more and may activate pumping mechanism driving circuit 106 to subsequently operate pumping mechanism 104 according to the input operation point parameters. Sensor output monitor 116 may initiate/enable sensor driving circuit 110 to subsequently enable or activate sensor 108 to detect initiation situations such as free flow, air bubbles, flow rate, conclusion of priming and more. Sensor output monitor 116 may receive feedback from sensor 108 via sensor driving circuit 110 and may modify pumping mechanism 104 via pumping mechanism control 114, for example disable pumping mechanism 104 if free flow is detected.

According to some embodiments, during a pumping mode, pumping mechanism control 114 may continuously activate pumping mechanism 104 via pumping mechanism driving circuits 106 according to predefined input operation parameters (flow rate, length of treatment and more). Sensor output monitor may receive feedback from sensor 108 and notify when an unwanted situation is sensed such as free flow, higher or lower than expected flow rate, air bubbles are detected and more. Sensor output monitor 116 may optionally, utilize the feedback from sensor 108 to adjust pumping mechanism circuits 106 so that pumping mechanism 104 pumps fluid through an associated tube according to the predefined input operation parameters. For example, if an input parameter is defined so that pumping mechanism 104 pumps fluid through an associated tube at a given rate, however sensor 108 sends feedback to sensor output monitor 116 that the flow rate is lower than expected then pumping mechanism control 114 may adjust pumping mechanism driving circuits 106 to correct the operation of pumping mechanism 104 so that the given rate is achieved.

According to some embodiments, during decalibration testing a predefined test with predetermined action may be implemented on infusion pump 102, resulting in a characteristic which may be sensed at sensor 108 or triggered by sensor 108 and may be compared by decalibration detector 118 to a range of acceptable values for that test.

According to some embodiments, in a decalibration testing mode to check improper functioning or decalibration of infusion pump 102, wherein in this example sensor 108 is a bubble detector, a predetermined amount of air bubbles may be inserted into a tube associated with infusion pump 102. If the air bubbles are detected by sensor 108, then decalibration detector 118 may recognize that sensor 108, air bubble detector in this example, is intact and/or that infusion pump 102 is calibrated and/or in need of recalibration.

According to some embodiments, in a decalibration testing mode to check improper functioning or decalibration of infusion pump 102, wherein in this example sensor 108 is a pressure sensor, a predetermined pressure may be applied, optionally, proximal to the end of a tube associated with infusion pump 102. The change in pressure may be detected by sensor 108, then decalibration detector 118 may recognize if the pressure sensed at sensor 108 is in accordance with a predefined table of expected changes in pressure and accordingly, determine if infusion pump 102 is calibrated and/or in need of recalibration.

According to some embodiments, in a decalibration testing mode to check improper functioning or decalibration of pump 102, wherein in this example sensor 108 is a flow-rate sensor, the infusion pump may be activated so that pumping mechanism 104 is operated so that a specific flow rate of fluid is expected in a tube associated with infusion pump 102. Actual flow rate may be detected by sensor 108, then decalibration detector 118 may recognize if the achieved flow rate at sensor 108 is in accordance with a predefined range of flow rates and accordingly, determine if infusion pump 102 is calibrated and/or in need of recalibration.

According to some embodiments, in a decalibration testing mode to check improper functioning or decalibration of pump 102, wherein in this example sensor 108 is a pressure sensor or air detector, the infusion pump may be activated so that pumping mechanism 104 is operated so that a specific flow rate of fluid is expected in a tube associated with infusion pump 102. Pumping mechanism controller 114 may count or store the number of cycles or number of drops emitted by the pump or length of time the test is active. Sensor 108 may sense when an occlusion is detected at the end of the tube signaling that a container connected to the tube is full or may sense air has entered into the system signaling that the reservoir is empty. Decalibration detector 118 may calculate the average or estimated flow rate, recognize if the achieved flow rate at sensor 108 is in accordance with a predefined range of flow rates and accordingly, determine if infusion pump 102 is calibrated and/or in need of recalibration.

According to some embodiments, an additional or supplemental sensor to sensor 108 may be added such as an external sensor to initiate a termination signal to indicate that the test has concluded and flow rate/accuracy should be calculated. For example a sensor at the reservoir can indicate it is empty or a sensor at the container can indicate that it is full or otherwise. Decalibration detector 118 may receive the termination signal and calculate the flow rate or accuracy accordingly.

According to some embodiments, decalibration detector 118 may determine if infusion pump 102 is calibrated and/or in need of recalibration in accordance with one or more predefined tests such as bubble detection, pressure sensing, flow rate, flow accuracy and more.

According to some embodiments, controller 112 may relay results of a decalibration test to an external server, for example so that results of several pumps can be stored for statistical purposes, so that an external party can monitor intactness of one or more infusion pumps and more.

According to some embodiments, Controller 112 may be a single or multiple controllers and sensor output monitor 116, pumping mechanism 114 and decalibration detector 118 may be onboard, embedded together or otherwise.

Figure 1B:
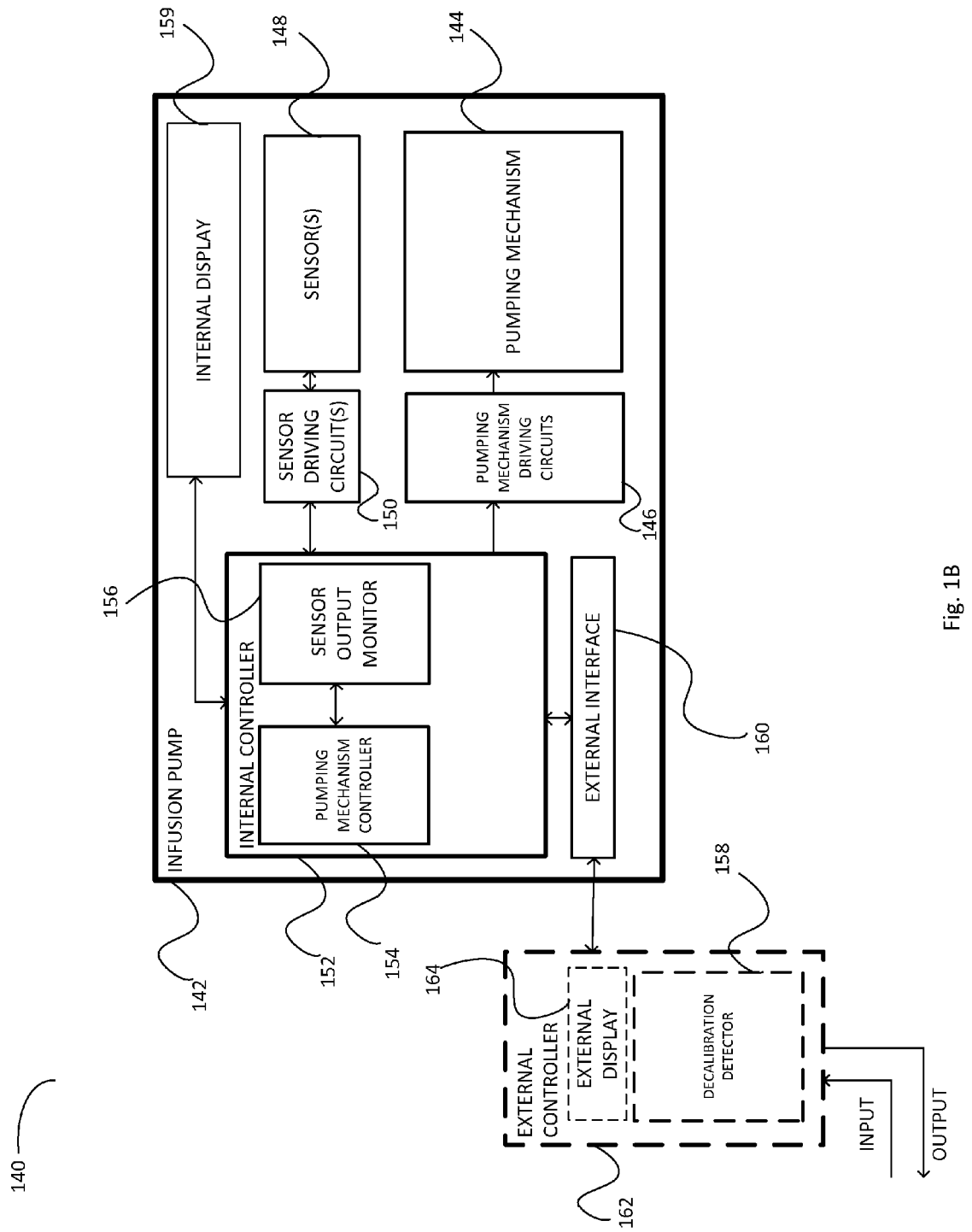
FIG. 1B is a functional block diagram of an exemplary infusion system according to some embodiments of the present invention where decalibration testing is achieved in conjunction with control circuitry connected to the pump through an external interface.

Turning now to FIG. 1B depicted is a functional block diagram of an exemplary infusion pump (140), according to some embodiments where decalibration testing is achieved in conjunction with control circuitry connected to the pump through an external interface such as external controller 162. It is understood that elements 142-156 and 159 are substantially similar to elements 102-116 and 119 (accordingly) of FIG. 1A as well as the interaction between these elements as described above. Infusion pump 142 may further include external interface 160 configured to receive information from and relay sensor feedback to an external decalibration detector such as decalibration detector 158. External interface 160 may further enable receiving test information According to some embodiments, during a decalibration testing a predefined test with predetermined action may be implemented on infusion pump 142, resulting in a characteristic which may be sensed at sensor 148 or triggered by sensor 148 and may be relayed to external decalibration detector 158 via external interface 160 and compared at external decalibration detector 158 to a range of acceptable values for that test. Furthermore, internal controller may receive input from external controller 162 with operation parameters or inputs to activate and carry out decalibration test modes. Decalibration testing results may further be stored in external controller 162, relayed to and stored within internal controller 152 and/or relayed to an external server. External controller 162 may be embedded in a PC, hand-held device, dedicated circuitry or otherwise.

According to some embodiments, external controller 162 may further include an external display such as external display 164 which may be a LCD display, LED display, touchscreen, or otherwise and may be configured to be an output device to display messages and information from external controller 162 as well as an input device to receive input information from a user or technician and relay the received information or parameters to external controller 162.

According to some embodiments, in a decalibration testing mode to check proper functioning of infusion pump 142, wherein in this example sensor 148 is a flow-rate sensor, infusion pump 142 may be activated by inputs received via external interface 160 so that pumping mechanism 144 is operated so that a specific flow rate of fluid is expected in a tube associated with infusion pump 142. Actual flow rate may be detected by sensor 148, then decalibration detector 158 may recognize if the achieved flow rate at sensor 148 is in accordance with a predefined range of flow rates and accordingly, determine if infusion pump 142 is calibrated or in need of recalibration.

According to some embodiments, in a decalibration testing mode to check proper functioning of infusion pump 142, wherein in this example sensor 148 is a pressure sensor, infusion pump 142 may be activated by inputs received via external interface 160 so that pumping mechanism 144 is operated so that a specific flow rate of fluid is expected in a tube associated with infusion pump 142. Pumping mechanism controller 154 may count or store the number of cycles of pumping mechanism 144 or number of drops emitted by pumping mechanism 144. A container may be connected at the distal end of the tube/conduit and an end-of-tube/conduit (or distal end) occlusion may be detected by sensor 148, then decalibration detector 158 may calculate the average flow rate (for example, the total volume of the container divided by the time it took to fill or the number of cycles until occlusion or otherwise) and calculate/determine/recognize if the achieved flow rate is in accordance with a predefined range of flow rates and accordingly, determine if infusion pump 142 is calibrated or in need of recalibration According to some embodiments, internal controller 152 may be a single or multiple controllers and sensor output monitor 156, pumping mechanism 154 may be onboard, embedded together or otherwise. External controller 162 may be a single or multiple controllers and decalibration detector 118 may be onboard, embedded or otherwise connected to other elements of external controller 162.

Figure 2A:
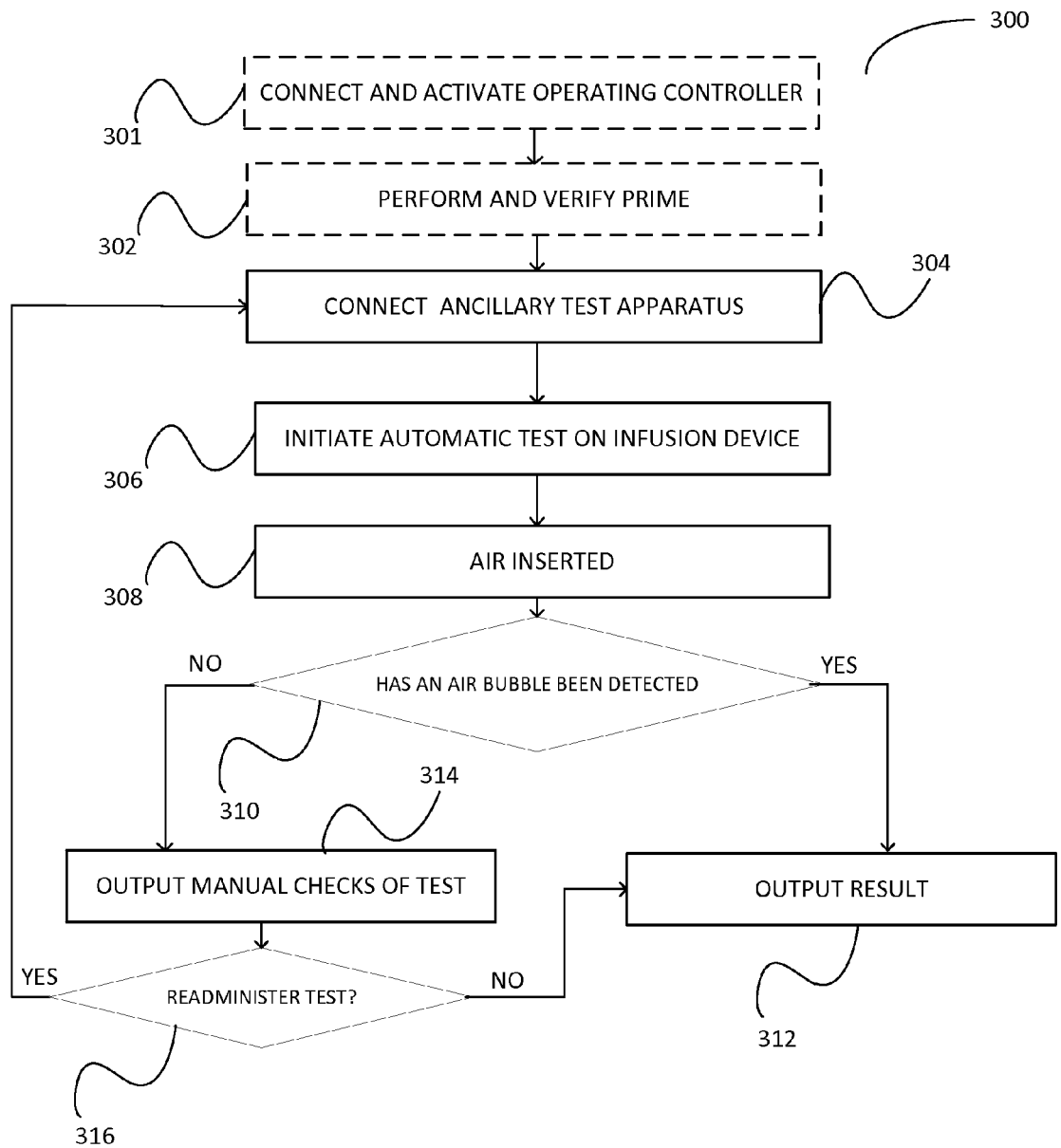
FIG. 2A is a flowchart including the steps of an exemplary method by which an infusion system according to some embodiments of the present invention may perform a decalibration test relating to bubble detection.
Figure 2B:
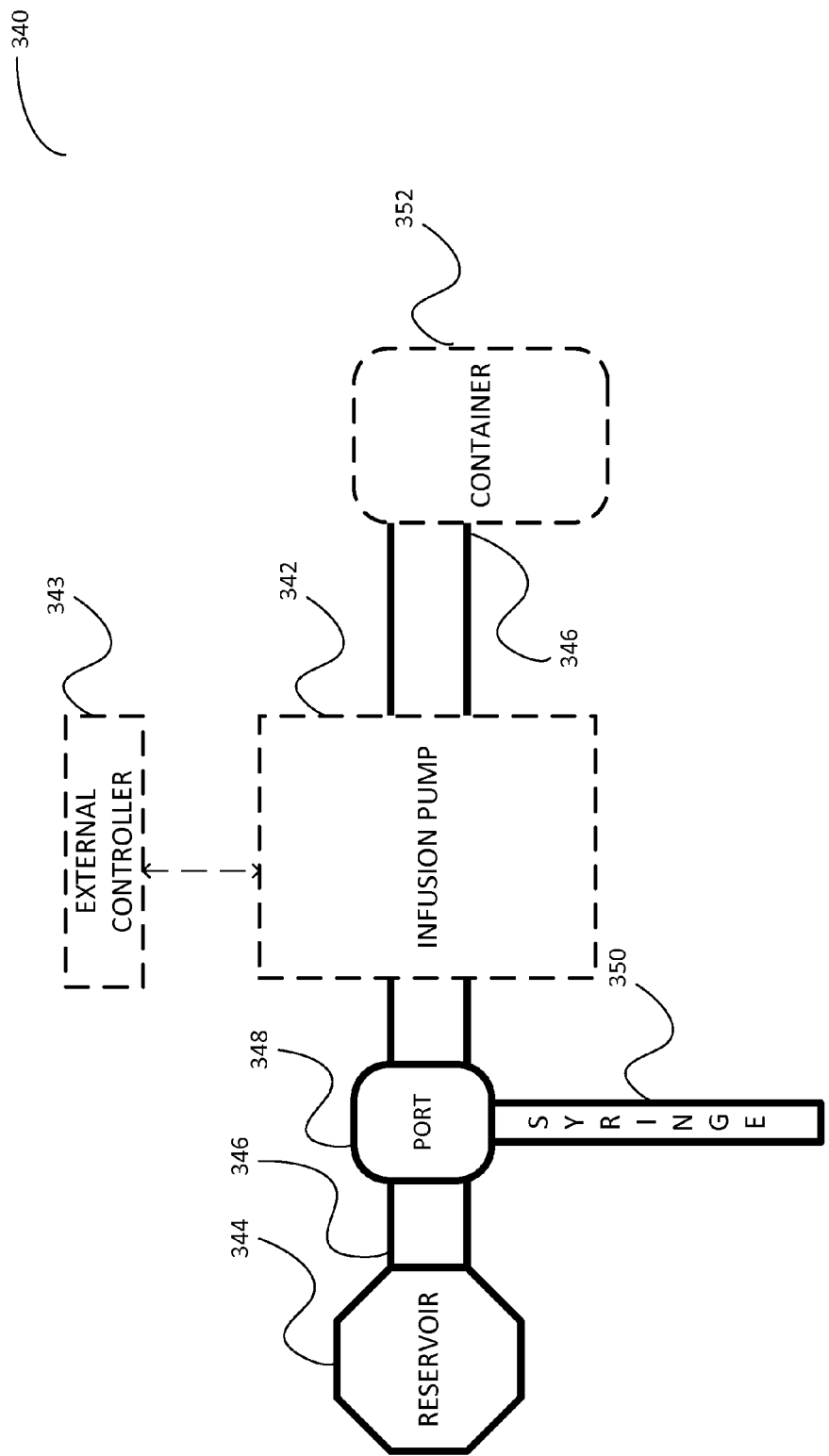
FIG. 2B is a functional block diagram showing an exemplary arrangement, including the pump and ancillary apparatus, with which an infusion system according to some embodiments of the present invention may perform a decalibration test relating to bubble detection.

Turning now to FIG. 2A, shown is a flowchart (300) including the steps of an exemplary method by which an infusion pump according to some embodiments of the present invention may perform a decalibration test relating to bubble detection. For clarity reference will also be made to FIG. 2B depicting is a functional block diagram showing an exemplary arrangement (340), including the pump and ancillary apparatus, with which an infusion pump according to some embodiments of the present invention may perform a decalibration test relating to bubble detection. Although the current embodiment describes a test running on one infusion pump it is understood that a controller may connect to one or more infusion pumps and the test may be run automatically on several pumps in parallel.

According to some embodiments, an operating controller to carry out the decalibration test may either be installed or activated on an internal controller of an infusion pump, such as infusion pump 342. Infusion pump 342 may optionally be connected or include an interface to an external controller such as external controller 343 which may at least partially control or initiate running of the test. A combination of internal and external controllers is also understood (step 301). Infusion pump 342 may further be associated or connected to an external server or configured to communicate with an external server.

According to some embodiments, arrangement 340 may include infusion pump 342 which may be connected to a reservoir such as reservoir 344 which may be, for example, a bag filled with water or saline or otherwise. A flexible tube such as conduit 346 may connect reservoir 344 to infusion pump 342. Arrangement 340 may further include an administration cassette or housing to mechanically connect conduit 346 to infusion pump 342, however many additional configurations may be applicable. Initially, when the 3 elements mentioned above (reservoir, infusion pump and conduit) are connected, priming of the arrangement and verification of priming (step 302) may be carried out to ensure that the arrangement is clean and/or prepared before experimentation, for example, ensuring that there is no air in the system. Step 302 may be carried out automatically by infusion pump 342, an external controller associated with infusion pump 342 or manually by a technician or user. Ancillary apparatus may now be connected to the arrangement (step 304) such as connecting a port such as port 348 to conduit 346 between reservoir 344 and infusion pump 342 and a syringe such as syringe 350 to conduit 346 via port 348. Port 348 may, for example, be a Y-connection or a spike with cap or otherwise. Syringe 350 may be a standard male-luer lock syringe or a female type syringe, a range of volumes of the syringe may be usable such as any syringe with a volume of 1-60 ml. Optionally, a container such as container 352 may be connected to the distal end of conduit 346 to receive any fluids flowing through arrangement 340.

According to some embodiments, step 304 may be removed/skipped/replaced by inserting air in a different manner into the system. For example, reservoir 344 may be flipped over so that air at the top of the reservoir enters conduit 346 or otherwise. In such an example the ancillary elements of FIG. 2B such as port 348 and syringe 350 may be unnecessary.

According to some embodiments, after the ancillary apparatus is connected (step 304) infusion pump 342 may be automatically activated to simulate or emulate normal activity of the pump (step 306), for example the pump may be activated at a predetermined rate such as 600 ml/hour, 100 ml/hour, 1 liter per hour or otherwise or optionally, a technician or user may be instructed to activate the pump at a predefined rate. Automatic activation of infusion pump 342 may optionally be initiated after air is inserted into the system as described below.

According to some embodiments, air may be inserted via syringe 350 to conduit 346 automatically by an electromechanical controller connected to the syringe or manually by a technician or user (step 308). A broad range of amounts of air to be inserted may be applicable and the exact amount of air may not be significant, but rather that the amount of air inserted is above a predefined threshold such as 0.1 ml, 1 ml, 5 ml or otherwise. The threshold of amount of air to be inserted may be defined so that it is substantially/significantly above the minimal resolution of air detection as determined by the specification and/or design of the relevant sensor in infusion pump 342. For example, the threshold amount of air to be inserted may be defined so that a detected air bubble is significant enough as not to be considered as background or accidental noise. If an air bubble is detected, the result is output (step 312) via a controller (internal or external to infusion pump 342) to the user (for example on a display associated with infusion pump 342) and/or may be relayed to an external server. The test result may be used either internally or externally to determine if infusion pump 342 requires recalibration or not. Along with the test results which may be relayed to an external server, the event log associated with infusion pump 342 may also be sent to the external server including actions and operations of infusion pump 342 which may be used to analyze statistical tests associated with infusion pump 342 and more infusion pumps, as well as study and analyze infusion pump 342 specifically.

According to some embodiments, if an air bubble has not been detected (step 310) for over a predetermined amount of time (For example 10 sec., 30 sec, 2 min. or 10 min.) infusion pump 342 may output manual checks to be confirmed such as: confirm if air was indeed inserted, confirm syringe 350 was indeed connected to the system and more (step 314). Manual tests and checks to determine if the test should be re-administered may be output to the user (step 316) for example, if air was not inserted or a different fault or mistake has occurred the test may be restarted (step 304), however if the test was administered unsuccessfully several times, or air has not been detected despite the test being administered correctly this result may be output as well (step 312).

Figure 3A:
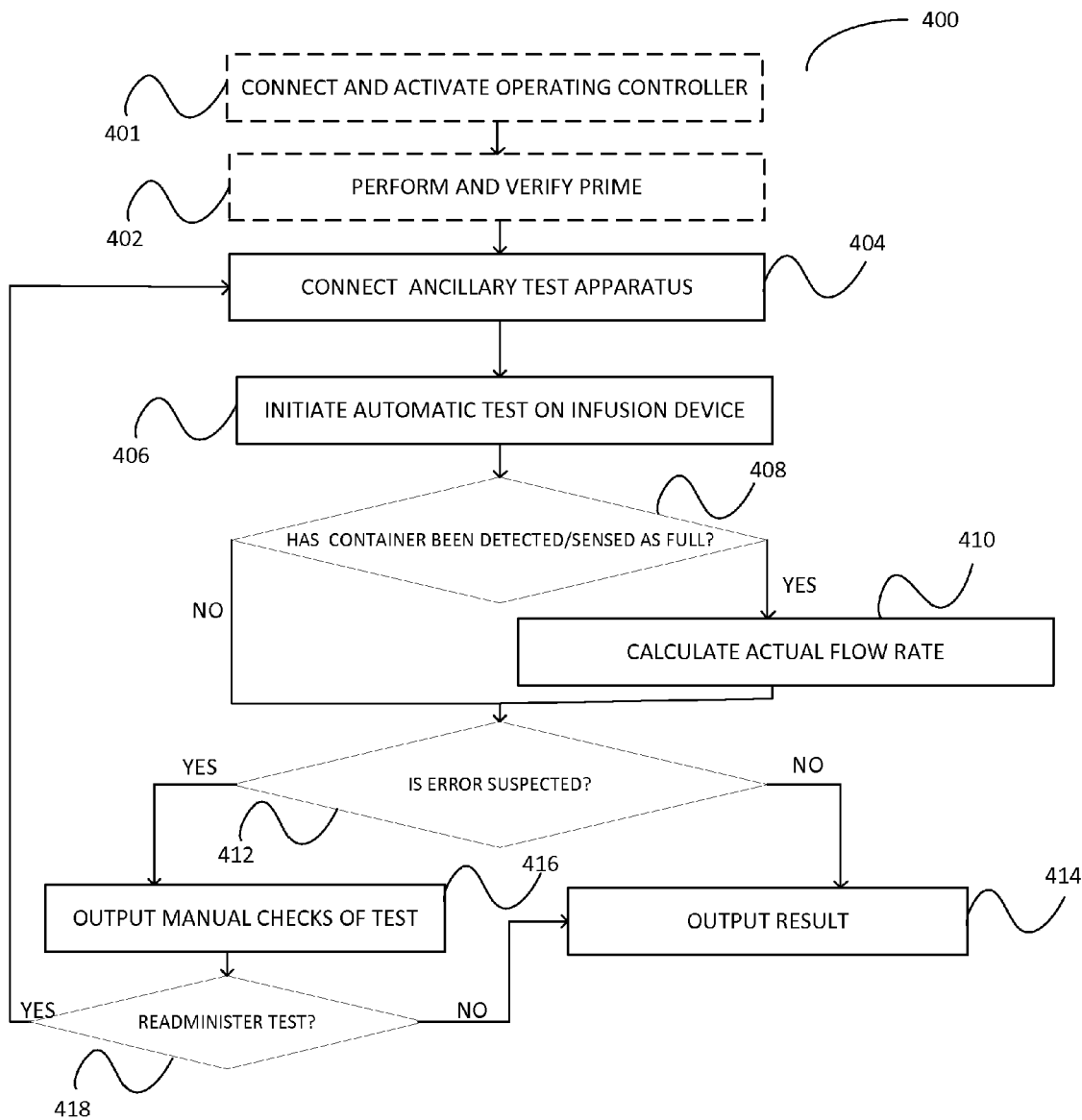
FIG. 3A is a flowchart including the steps of an exemplary method by which an infusion system according to some embodiments of the present invention may perform a decalibration test relating to flow rate.
Figure 3B:
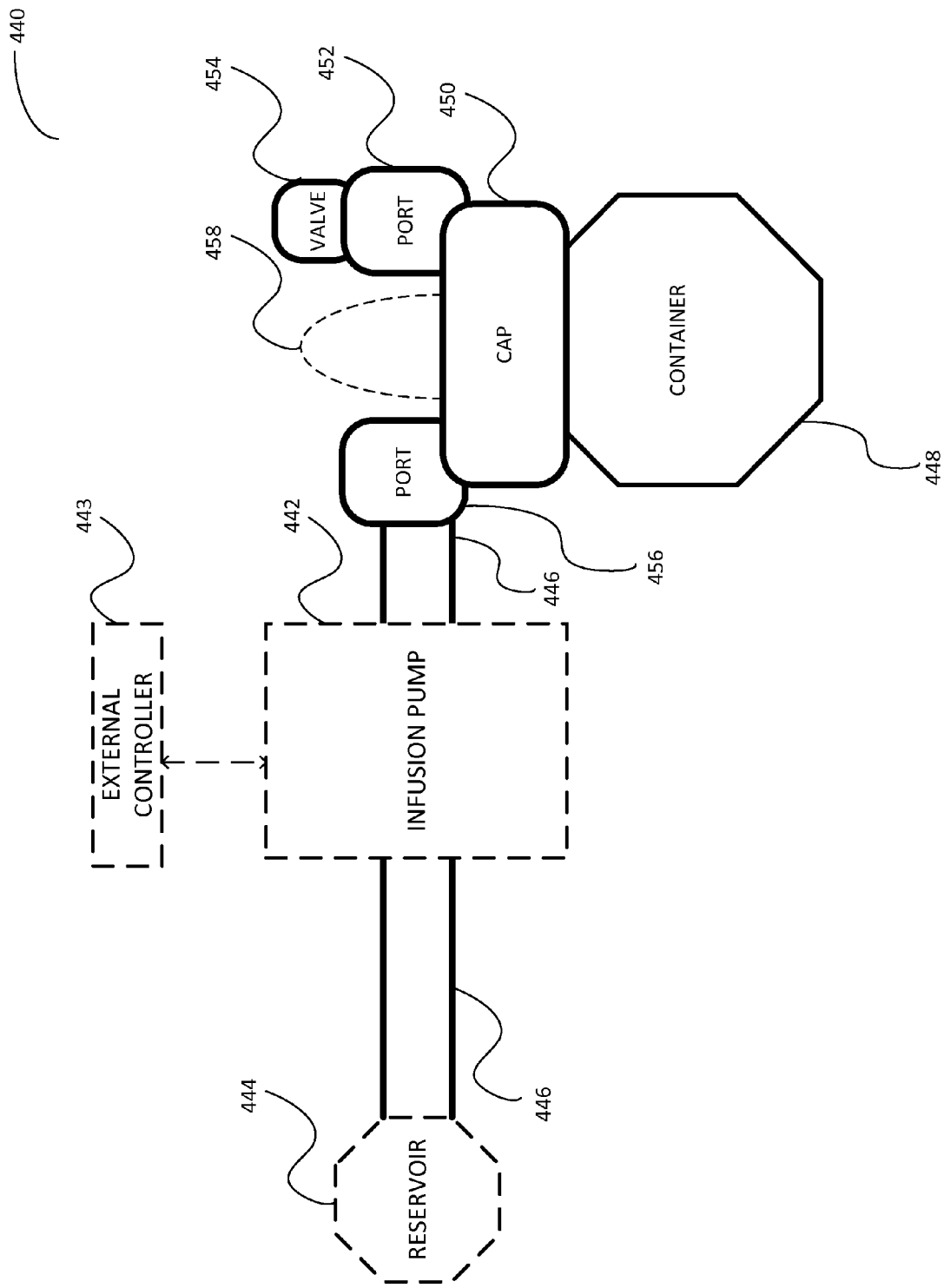
FIG. 3B is a functional block diagram showing an exemplary arrangement, including the pump and ancillary apparatus, with which an infusion system according to some embodiments of the present invention may perform a decalibration test relating to flow rate.

Turning now to FIG. 3A, shown is a flowchart (400) including the steps of an exemplary method by which an infusion pump according to some embodiments of the present invention may perform a decalibration test relating to flow rate. Reference will also be made to FIG. 3B depicting a functional block diagram showing an exemplary arrangement (440), including the pump and ancillary apparatus, with which an infusion pump according to some embodiments of the present invention may perform a decalibration test relating to flow rate. Elements 442-446 are understood to be substantially similar to elements 342-346 (accordingly) of FIG. 2B, and steps 401 and 402 are understood to be substantially similar to steps 301 and 302 (accordingly) of FIG. 2A.

According to some embodiments, after priming has been confirmed (step 402) ancillary apparatus for the flow rate test may be connected (step 404) to elements 442-446 of arrangement 440. Accordingly, a container of a predetermined total volume such as container 448 may be configured to receive fluids from reservoir 444 via infusion pump 442. Container 448 may optionally, be sealed with a cap such as cap 450, or may include a faucet or valve to enable subsequent draining or may not include either (for example if container 448 is a burette). For example, an exemplary container marked as a 120 ml container may actually be able to contain 131 ml when taking into account the volume in the neck of the bottle. Different sizes of containers can be utilized such as 50 ml, 200 ml, 400 ml, 1 liter or otherwise. Cap 450 may include 2 ports such as port 452 and port 456.

Port 452 may be connected to a vented valve such as valve 454 to ensure that air trapped in the container can be released so that the container can be completely filled with fluid. Valve 454 may be selected from a wide range of apparatuses allowing for air to be dispersed and liquid to be contained or locked within the container or otherwise. Valve 454 may further include a stem which may ensure minimal leaks from the attachment point. Valve 454 may be a disposable filter. Container 448 may be connected to conduit 446 via port 456. It is understood that port 456 and port 454 may be identical and as such may be interchangeable so that conduit 446 is connected to container 448 via port 452. Port 456 and port 454 may be positioned at an angle within a predetermined range so that easy handling (connecting and disconnecting) of valve 454 and conduit 456 may be achieved. Cap 450 may further include a hanger or hook such as hanger 458, to allow the container-cap assembly to be hung and positioned upright so that air in the container can be fully disperse and aid in keeping valve 454 dry.

According to some embodiments, once the ancillary circuitry has been connected an automatic test may be initiated on infusion pump 442 (step 406). Accordingly, the pump may run at a predetermined rate (such as 300 ml/hr, 600 ml/hr, 1 liter/hr or otherwise). If container 448 is detected as full (step 408) accordingly, the estimated or average flow rate is calculated (for example by dividing the fluid container volume by the amount of time it took to be filled/number of cycles infusion pump 442 has concluded for the downstream occlusion to be detected).

According to some embodiments, container 448 may be detected as full if an occlusion is detected downstream, a fluid sensor associated with container 448 may signal that fluid has reached a predefined volume. Additional termination criteria can be designed to electronically signal that a predefined volume has passed through infusion pump 442 and an average flow rate may be calculated (step 410) and the result is output (step 312) via a controller (internal or external to infusion pump 442) to the user.

According to some embodiments, if the calculated flow rate is substantially different from the expected flow rate (the predetermined flow rate at which infusion pump 442 was activated) or if no occlusion was detected within a predetermined time frame or if an error in the test is otherwise suspected (step 412) then manual checks to be carried out may be output on a display associated with infusion pump 442 (step 416). For example, if an occlusion was detected substantially earlier than expected, a technician or user may be asked to verify that valve 454 is not wet or jammed and that container 448 is positioned upright. In another example, if an occlusion was not detected in a predetermined time frame, a user or technician may be instructed to verify that neither the container nor the valve are leaking and that conduit 446 is indeed connected to container 448 via port 456. Based on user's input as well as additional information (amount of times the test has failed, and more) it may be determined if the test needs to be re-administered or not (step 418). If the test need not be re-administered then the results are output (step 414) similar to step 312 of FIG. 2A. Otherwise, the test may be re-administered (step 404).

Figure 4A:
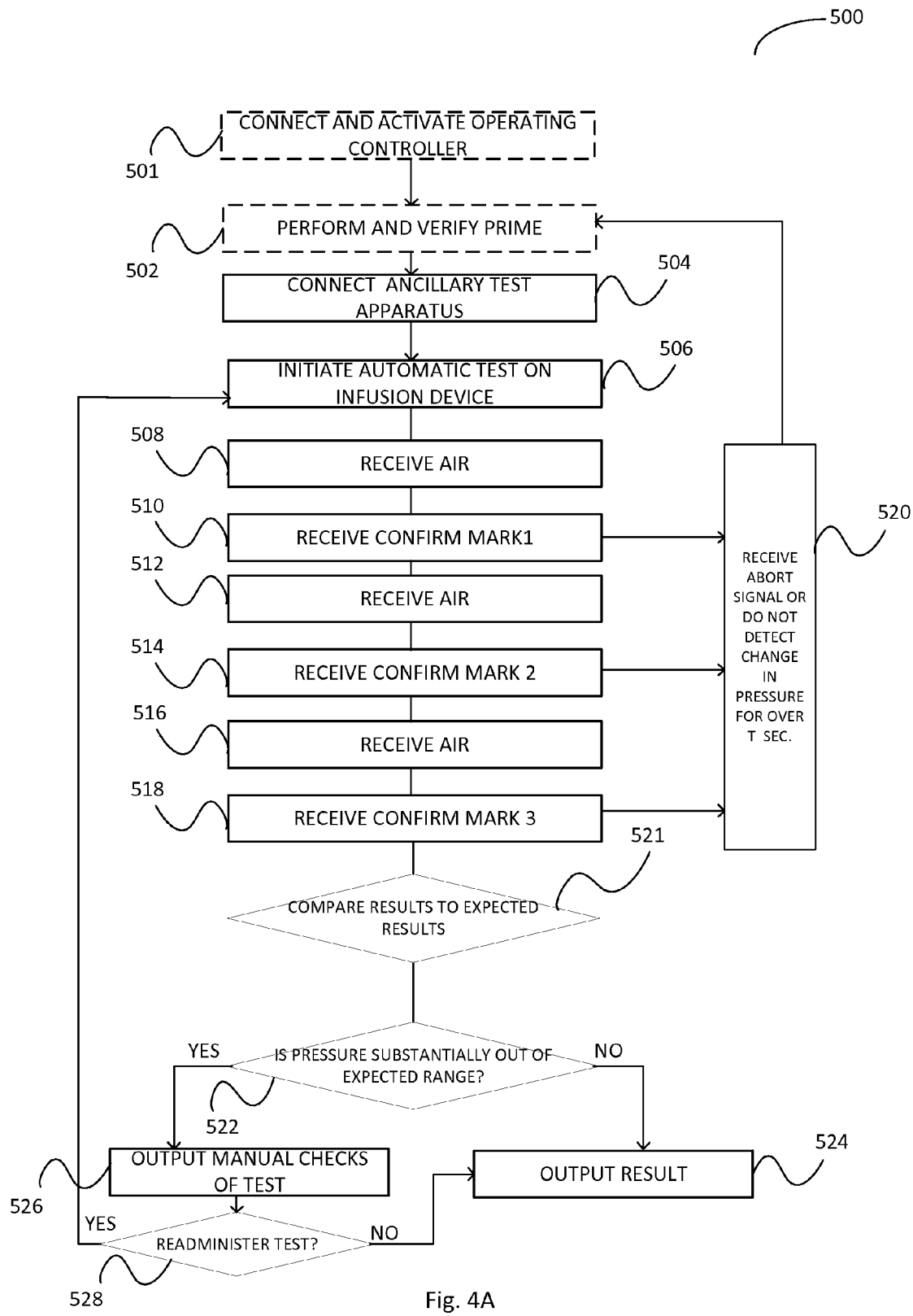
FIG. 4A is a flowchart including the steps of an exemplary method by which an infusion system according some embodiments of the present invention may perform a decalibration test relating to fluid pressure.
Figure 4B:
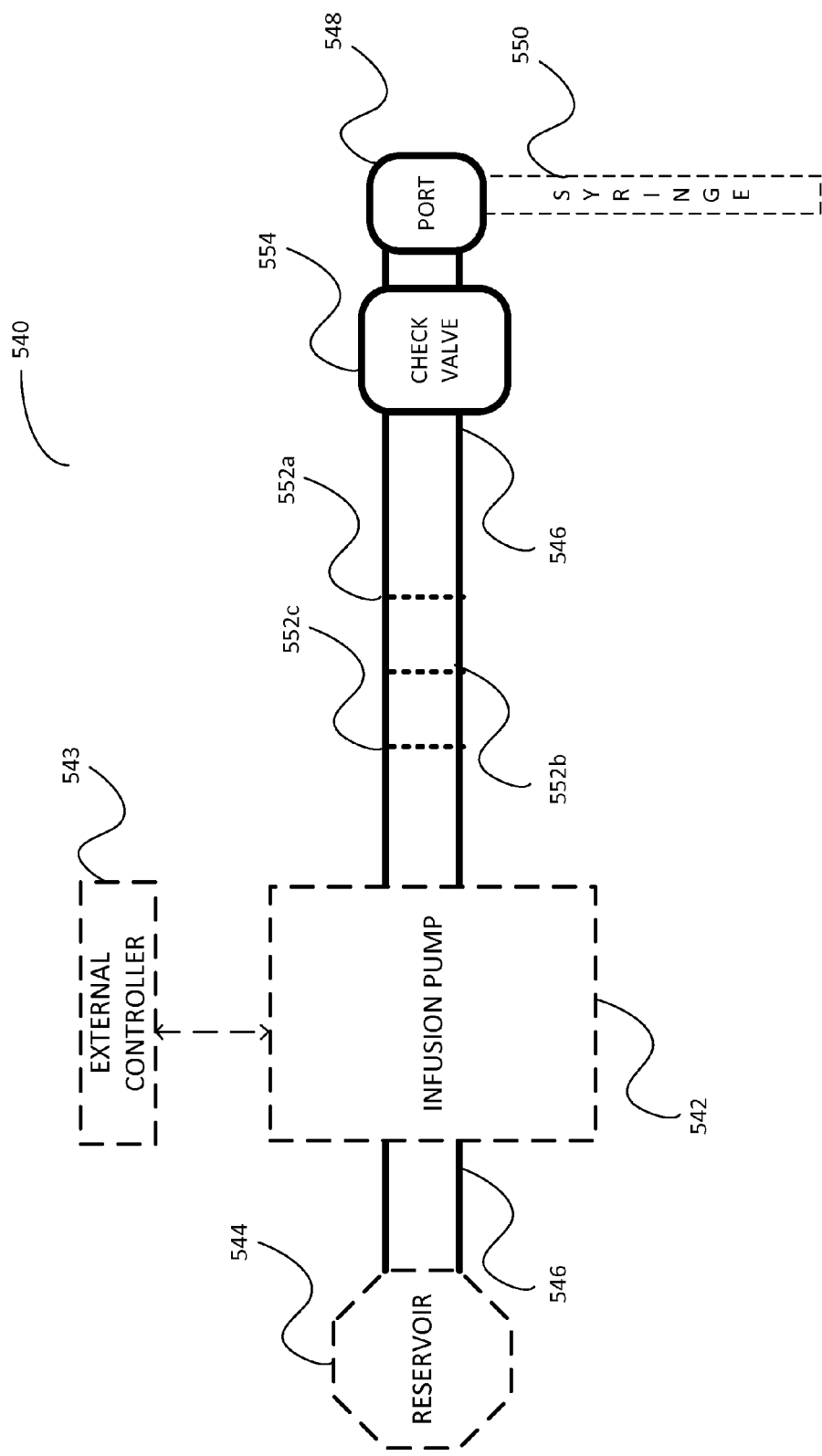
FIG. 4B is a functional block diagram showing an exemplary arrangement, including the pump and ancillary apparatus, with which an infusion system according to some embodiments of the present invention may perform a decalibration test relating to fluid pressure.

Turning now to FIG. 4A, shown is a flowchart (500) including the steps of an exemplary method by which an infusion pump according some embodiments of the present invention may perform a decalibration test relating to fluid pressure. Reference will also be made to FIG. 4B depicting a functional block diagram showing an exemplary arrangement, including the pump and ancillary apparatus (540), with which an infusion pump according to some embodiments of the present invention may perform a decalibration test relating to fluid pressure. Elements 542-550 are understood to be substantially similar to elements 342-350 (accordingly) of FIG. 2B, and steps 501 and 502 are understood to be substantially similar to steps 301 and 302 (accordingly) of FIG. 2A. According to some embodiments, after priming has been confirmed (step 502) ancillary apparatus for the fluid pressure test may be connected (step 504) to elements 542-546 of arrangement 540. Accordingly, a check valve such as check valve 554 may be connected to or embedded within conduit 546. Additional ports or connectors may be utilized to connect or attach check valve 554 to conduit 546. A pressure inducer, which in an exemplary embodiment may be substantially similar to syringe 350 of FIG. 2B may be connected to check valve 554 via a port such as port 548. Check valve 554 may be configured to ensure that air, gas, oil and/or any other pressure inducing material or substance which can be distinguished from the liquid emitted from reservoir 544 can be pushed/pressured/pressed into conduit 546 but cannot be released from conduit 546 via check valve 554. Optionally, check valve 554 may be selected or configured so that only when placed correctly syringe 550 can connect to it, for example if syringe 550 is male-type then check valve 554 may be chosen so that when positioned correctly (air is allowed to enter but not exit) syringe 550 can be connected. Furthermore, although a configuration including check valve 554 is preferable, flowchart 500 may be carried out without check valve 554. Optionally, syringe 550 may be a one-directional syringe to prevent pressure from releasing via the syringe.

According to some embodiments, an at least partially automatic test on infusion device may be initiated (step 506) so that infusion pump 542 is configured to operate in a pressure test mode (for example, activate pressure sensor and more). Syringe 550 may be utilized to insert air into conduit 546. A user or technician may be instructed to insert air into conduit 546 until air reaches a first mark on conduit 546 such as mark 552a (step 508) after which the user/technician may confirm this action (step 510). Accordingly, the user/technician may repeat this sequence (insert air and confirm) several times, for example, a total of three iterations (steps 512-518). Each mark may be determined or set in a way that insertion of air up to that line is expected to generate a predetermined pressure rise in conduit 546, (providing the test was setup correctly, for example conduit 546 was primed at beginning of test). The pressure rise may be derived from the measurements of conduit 546 and the spaces between marks 552a, 552b and 552c.

According to some embodiments, Infusion pump 542 may compare the measured differences in the detected pressure in the infusion pump to expected differences in an associated look-up table or map (step 521). During execution of the test (step 508-518) if a user or technician did not insert air within a predetermined time T, or they missed the mark or do not confirm reaching the mark or otherwise decide to abort the specific test (step 520) then the test may be restarted (step 502). Predetermined time T may be, for example, 30 seconds, 1 minute, 2 minutes or otherwise. If the measured results vary substantially from the expected results (step 522), infusion pump 542 may output onto an associated display a list of checks/tests and verifications (step 526) for example: verify that check valve 554 is in the correct direction, confirm there is no leaking, that air has indeed been inserted into the system and the amount of cycles the results are unsatisfactory. If the results are satisfactory (within a predefined range, close to the predefined range or the retesting is not required (step 528)) the results may be output (step 524). Step 524 is understood to be substantially similar to step 312 of FIG. 2A. If the additional or re-running of the test is required than the test may be re-started (step 502).

According to some embodiments, the sequences described above in FIGS. 2A, 3A and 4A may be carried out in sequence and/or modified to be carried out in sequence and additional tests may be understood. The final result determining if recalibration is needed may be defined by a combination of some or all of the output results of steps 312, 414 and 524 or by a single result. When carried out in sequence, some of the steps may be redundant, for example not all sequences may need to be initiated with priming or otherwise. The associated circuitry in FIGS. 2B, 3B and 4B may be modified so that the tests may be carried out in sequence. Additional elements for purposes of connectivity may be understood. Some elements for easy handling of the test may be added and choice of female or male ports may be designated based on connectivity to other elements. Accordingly a female type port may be chosen for a test utilizing a male type syringe.

According to some embodiments, an optimal sequence or order of administrating two or more of the tests described above may be considered preferable, for example, ensuring a pressure sensor is not decalibrated and then carrying out a flow rate test utilizing the pressure sensor may be preferable.

According to some embodiments, the ancillary apparatus of FIGS. 2B, 3B and/or 4B may be supplied separately or as a kit. Furthermore, a group of elements within the ancillary apparatus may be supplied as a kit while other elements (such as a reservoir, syringe) may be standard elements not supplied but assumed to be accessible to a user or technician in a regular environment (such as a hospital, medical care facility, home or otherwise). The ancillary apparatus may be disposable or limited in number of uses.

Figure 5:
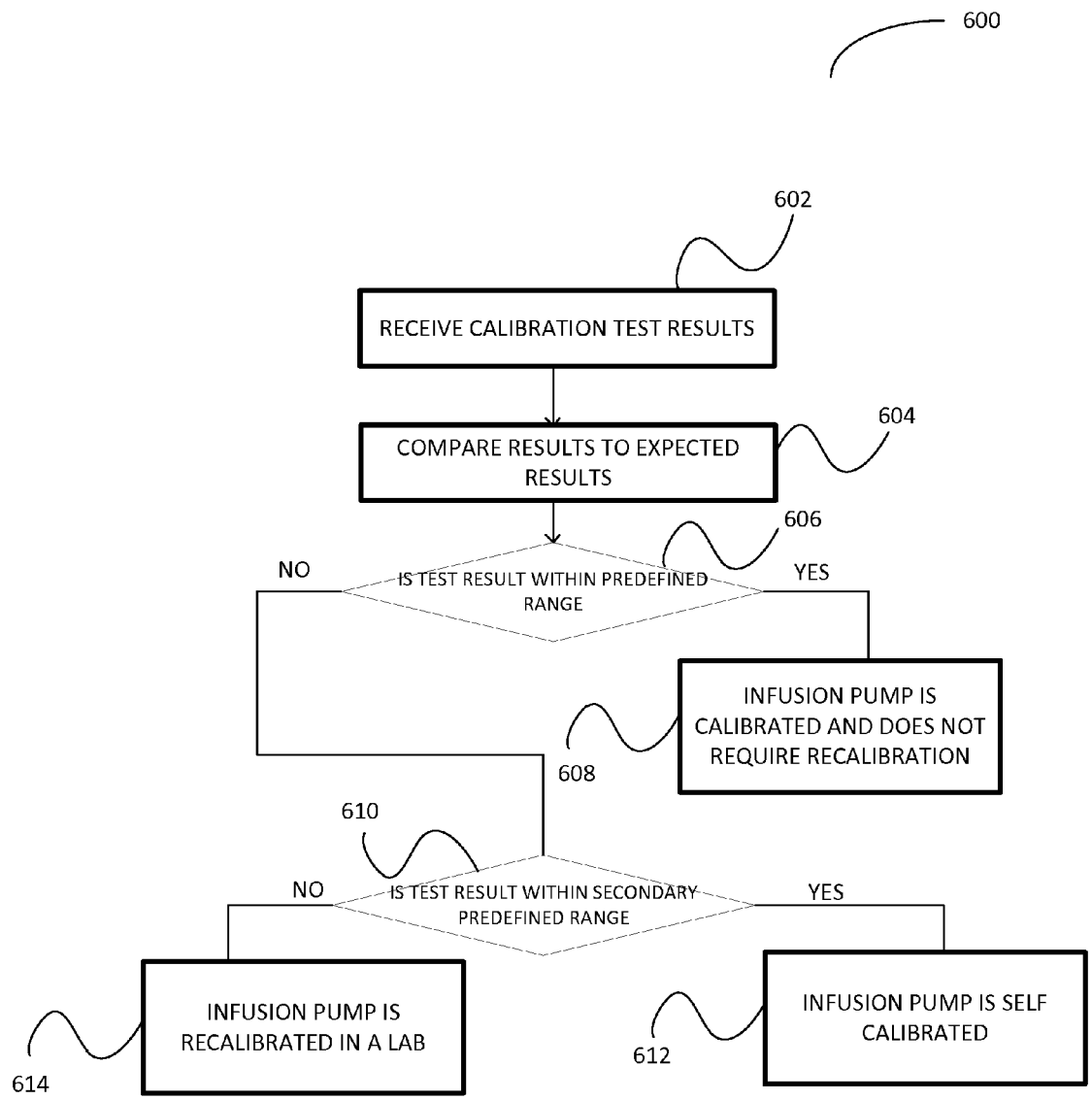
FIG. 5 is a flowchart including the steps of an exemplary method by which an infusion system according to some embodiments of the present invention may perform self-calibration based on decalibration test results.

Turning now to FIG. 5 shown is a flowchart (600) including the steps of an exemplary method by which an infusion pump according to some embodiments of the present invention may perform self-calibration based on decalibration test results. An infusion pump or associated control circuitry may receive or calculate/determine decalibration test results (602) and compare them with a range of acceptable and/or expected results (step 604). If the decalibration test results are within the range of acceptable results (step 606) then the pump may be designated as a calibrated pump and/or a pump that does not require recalibration (step 608) and can be returned to regular medical use of the pump. If the decalibration test results are not within the predefined acceptable range but are within a secondary allowable predefined range (step 610) then the pump may be self-calibrated (step 612). If the test results are outside of the secondary allowable predefined range then the infusion pump may be sent to a lab to be thoroughly recalibrated (step 614).

According to some embodiments, self-calibration may include: changing or updating parameters or lookup table(s) such as a look-up table of pressure measurements, look-up table of flow accuracy and/or parameters or coefficients of functions associated with one or more native sensors and/or perform automatic recalibration of an air-bubble detector.

According to some embodiments, a technician may input a code or identification to allow running of some or all of the decalibration tests. Identity of technician may be further stored in the pumping system.

While certain features of the invention have been illustrated and described herein, many modifications, substitutions, changes, and equivalents will now occur to those skilled in the art. It is, therefore, to be understood that the appended claims are intended to cover all such modifications and changes as fall within the true spirit of the invention.

What is claimed:

1. An infusion pump having a decalibration test mode to determine whether the infusion pump is decalibrated, said pump comprising:
    a native pumping mechanism to drive fluids through a functionally associated conduit at a predetermined first flow rate;
    at least one native sensor to sense a physical characteristic of the fluid within the conduit including a pressure sensor to sense a level of pressure of the fluid within the conduit and during said decalibration test mode to relay an indicator that a container, having a known volume connected to an output of said pumping mechanism, is full; and
    computing circuitry (a) to receive said indicator from said pressure sensor, (b) in response to receiving said indicator, to calculate an average flow rate at least partially based on said indicator and (c) to determine whether the infusion pump is decalibrated based on a comparison of said average flow rate with said predetermined first flow rate.

2. The infusion pump according to claim 1, further comprising an external interface for a decalibration testing device, which decalibration testing device does the comparison of the output to an expected decalibration test parameter.

3. The infusion pump according to claim 1, wherein said at least one native sensor further comprises a bubble detector.

4. The infusion pump according to claim 1, wherein said at least one native sensor further comprises a second sensor selected from the group consisting of: an accelerometer, a temperature sensor, an altitude sensor and a flow meter.

5. The infusion pump according to claim 1, wherein said native sensor is configured to detect that a predefined volume of fluid has passed through said native pumping mechanism.

6. The infusion pump according to claim 1, wherein said native pumping mechanism is classified by a unique identification and said computing circuitry is configured to store said unique identification and said decalibration testing result.

7. The infusion pump according to claim 1, further comprising a counter to relay a cycle number associated with said pumping mechanism and wherein said computing circuitry calculates said estimated flow rate based on said cycle number and the known volume.

8. An infusion pump decalibration testing system, comprising:
    a pumping mechanism to drive fluids through a functionally associated conduit at a predetermined first flow rate;
    at least one sensor to sense a physical characteristic of the fluid within the conduit, including a pressure sensor to sense a level of pressure of the fluid within the conduit and during a decalibration test mode to relay an indicator that a container, having a known volume connected to an output of said pumping mechanism, is full;
    computing circuitry having a decalibration test mode (a) to receive said indicator from said pressure sensor during the decalibration test mode, (b) in response to receiving said indicator, to calculate an average flow rate at least partially based on said indicator and (c) to determine whether the infusion pump is decalibrated based on a comparison of said average flow rate with said predetermined first flow rate; and ancillary circuitry to activate a predetermined state on said pumping mechanism including said container.

9. The testing system of claim 8, wherein said predetermined state is selected from the group consisting of: inserting air above a predefined threshold within said pumping mechanism, external pressure on said pumping mechanism.

10. The system according to claim 8, wherein said at least one sensor includes a bubble detector.

11. The system according to claim 8, wherein said ancillary circuitry further comprises a syringe, a check valve and a predefined line-marked conduit.

12. The system according to claim 8 wherein said ancillary circuitry is a container having a known volume capacity, wherein said container is connectable to said conduit and a valve.

13. The testing system of claim 8, further comprising a counter to relay a cycle number associated with said pumping mechanism and wherein said computing circuitry calculates said estimated flow rate based on said cycle number and the known volume.

* * * * *